(12) United States Patent
Linder et al.

(10) Patent No.: US 12,201,337 B2
(45) Date of Patent: Jan. 21, 2025

(54) EXPANDABLE LAMINOPLASTY DEVICE

(71) Applicant: Curiteva, Inc., Tanner, AL (US)

(72) Inventors: Eric Linder, Columbus, OH (US);
Ryan Heskett, Wellington, FL (US)

(73) Assignee: Curiteva, Inc., Tanner, AL (US)

( * ) Notice: Subject to any disclaimer, the term of this patent is extended or adjusted under 35 U.S.C. 154(b) by 0 days.

(21) Appl. No.: 18/411,381

(22) Filed: Jan. 12, 2024

(65) Prior Publication Data
US 2024/0138893 A1 May 2, 2024

Related U.S. Application Data

(62) Division of application No. 17/824,110, filed on May 25, 2022, now Pat. No. 11,918,265, which is a division of application No. 17/010,269, filed on Sep. 2, 2020, now Pat. No. 11,376,052.

(51) Int. Cl.
*A61B 17/70* (2006.01)
*A61B 17/80* (2006.01)
*A61B 17/88* (2006.01)
A61B 17/56 (2006.01)

(52) U.S. Cl.
CPC ...... *A61B 17/8852* (2013.01); *A61B 17/7059* (2013.01); *A61B 17/8004* (2013.01); *A61B 2017/564* (2013.01)

(58) Field of Classification Search
CPC ............ A61B 17/7071; A61B 17/8004; A61B 17/8852; A61B 17/025; A61B 17/66; A61B 17/663; A61B 17/666; A61B 17/7001; A61F 2/44; A61F 2/443; A61F 2002/30523; A61F 2002/30525
See application file for complete search history.

(56) References Cited

U.S. PATENT DOCUMENTS

| | | | |
|---|---|---|---|
| 2,453,656 A * | 11/1948 | Bullard | F16H 19/04 74/462 |
| 4,636,217 A * | 1/1987 | Ogilvie | A61F 2/44 606/247 |
| 5,470,333 A | 11/1995 | Charles | |
| 5,664,457 A * | 9/1997 | Nejati | F16H 19/04 74/89.17 |
| 6,126,660 A * | 10/2000 | Dietz | A61B 17/025 606/90 |
| 7,018,415 B1 | 3/2006 | McKay | |
| 7,264,620 B2 | 9/2007 | Taylor | |
| 7,695,473 B2 | 4/2010 | Ralph et al. | |
| 7,883,532 B2 | 2/2011 | Biscup et al. | |
| 7,909,870 B2 | 3/2011 | Kraus | |

(Continued)

*Primary Examiner* — Anu Ramana
(74) *Attorney, Agent, or Firm* — Bookoff McAndrews, PLLC

(57) ABSTRACT

An expandable laminoplasty device has a superior plate, an inferior plate, threaded or racked gear post having external threads or gear teeth, the post affixed to one of the superior plate or the inferior plate, and a gear nut or pinion gear, the gear has internal threads or external gear teeth configured to engage external threads or gear teeth of the post. The gear is held in one of the superior plate or inferior plate not affixed to the post and wherein the superior plate or inferior plate not affixed to the post has an end with a slot or channel to receive the post and a side opening to receive and hold the gear.

5 Claims, 22 Drawing Sheets

(56) References Cited

U.S. PATENT DOCUMENTS

| | | | |
|---|---|---|---|
| 8,128,663 B2 * | 3/2012 | Zucherman | A61K 31/37 606/249 |
| 8,147,528 B2 | 4/2012 | Mazucca et al. | |
| 8,172,875 B2 * | 5/2012 | Taylor | A61B 17/7071 606/246 |
| 8,262,710 B2 | 9/2012 | Freedman et al. | |
| 8,377,140 B2 * | 2/2013 | DeFalco | A61F 2/4611 254/98 |
| 8,562,681 B2 * | 10/2013 | Shepard | A61B 17/808 623/17.11 |
| 8,568,482 B2 | 10/2013 | Kraus | |
| 9,364,335 B2 | 6/2016 | Farin | |
| 9,480,503 B2 | 11/2016 | Khanna | |
| 9,486,253 B2 | 11/2016 | Millhouse et al. | |
| 9,808,350 B2 | 11/2017 | Shepard et al. | |
| 9,974,590 B2 | 5/2018 | Farin | |
| 10,226,284 B2 * | 3/2019 | Suh | A61B 17/7044 |
| 10,369,008 B2 | 8/2019 | Jimenez | |
| 10,543,024 B2 * | 1/2020 | Lee | A61B 17/7083 |
| 11,090,166 B2 * | 8/2021 | Tacca | A61B 17/7053 |
| 11,273,046 B2 | 3/2022 | Dewey | |
| 12,127,947 B2 * | 10/2024 | Tacca | A61B 17/7071 |
| 2010/0057127 A1 | 3/2010 | McGuire et al. | |
| 2010/0198221 A1 | 8/2010 | Hearn | |
| 2011/0046680 A1 * | 2/2011 | Khanna | A61B 17/7071 606/279 |
| 2012/0165942 A1 * | 6/2012 | Khanna | A61B 17/7071 623/17.16 |
| 2013/0060283 A1 * | 3/2013 | Suh | A61B 17/7007 606/246 |
| 2013/0226249 A1 * | 8/2013 | Konieczynski | A61B 17/808 606/282 |

* cited by examiner

EXPANDABLE LAMINOPLASTY DEVICE

RELATED APPLICATIONS

The present invention is a division of U.S. application Ser. No. 17/824,110 filed on May 25, 2022 which is a division of U.S. application Ser. No. 17/010,269 filed on Sep. 2, 2020 entitled, "Expandable Laminoplasty Device", now U.S. Pat. No. 11,376,052 issued on Jul. 5, 2022.

FIELD OF THE INVENTION

The present invention relates to an improved device for use in a laminoplasty procedure, more particularly, a continually adjustable expandable laminoplasty device is disclosed in several embodiments employing a gear mechanism to adjust the distance between a superior plate and a lower or inferior plate.

BACKGROUND OF THE INVENTION

Arthritis in the cervical spine can lead to narrowing of the spinal canal at multiple levels throughout the neck. When the narrowing becomes severe, it can lead to compression of the spinal cord, referred to as "myelopathy."

Corrective surgical procedures have one goal which is to take pressure off the spinal cord and create more space in the spinal canal. When the disease is only present at only one or two levels, a procedure commonly performed is called, "Anterior Cervical Decompression and Fusion (ACDF)." The surgeon removes the disc and bone spurs compressing the spinal cord from the front of the neck and then fuses the two levels together.

A "fusion" procedure relies on bone formation between two spinal levels until they are united. This process can take up to 6 months to be completely solid or "healed." When a fusion fails to heal after 8-12 months, this is then considered a "non-union". Some surgeons prefer to take pressure off the spinal cord from the back of the neck when three or more levels of compression are involved.

To take pressure off the spinal cord from the back of the neck, the surgeon must remove portions of the bones, called "laminectomy," which creates more space for the spinal cord. Because the removal of these bones disrupts the attaching ligaments and structures in the neck, this can cause a gradual neck deformity or instability. To help prevent this from occurring, laminectomy is combined with a fusion procedure using screws and rods to hold the vertebral segments together until bone grows and fuses them to one another.

Arthritis in any joint, including the spine, can cause significant pain with motion. Because spinal cord compression and myelopathy typically occur in the setting of advanced arthritis, the elimination of motion with a fusion procedure also may help decreased pain associated with arthritis in the spine. However, there are some patients who have evidence of spinal cord compression at multiple levels with myelopathy, but do not complain of any neck pain. These patients may be good candidates for cervical laminoplasty.

Cervical laminoplasty, a procedure first described in Asia, involves creating more space for the spinal cord while avoiding fusion and maintaining spinal motion. Several different types of procedures have been described, but they all involve the same basic concepts. The surgeon cuts a portion of the lamina bone all the way through allowing the spinal canal to be enlarged. The lamina forms a rigid roof over the spinal canal, a laminoplasty effectively props that roof open thus enlarging the spinal canal. This procedure is performed from the back of the neck and involves creating an "opening door hinge" with the bones to create more space for the spinal canal instead of removing portions of the bones as done with laminectomy, thus avoiding disruption of some of the supporting structures. Small plates and screws have been designed to hold open the door-hinge and maintain the increased space for the spinal canal. The spinal segments are not fused together, and post-operative motion is encouraged to avoid any residual stiffness following the procedure.

Cervical laminoplasty procedures have employed plates for maintaining the opening at a desired distance. Many patents have been granted on such devices. Most laminoplasty plates are not adjustable in length. A few are adjustable in increments.

The present invention, as described hereinafter, provides a continuously adjustable length capability giving the surgeon the ability to optimally set the device.

SUMMARY OF THE INVENTION

An expandable laminoplasty device has a superior plate, an inferior plate, threaded post having external threads, the threaded post affixed to one of the superior plate or the inferior plate, and a gear nut, the gear nut has internal threads configured to engage external threads of the threaded post. The gear nut is held in one of the superior plate or inferior plate not affixed to the threaded post and wherein the superior plate or inferior plate not affixed to the threaded post has an end with a slot or channel to receive the threaded post and a side opening to receive and hold the gear nut. Rotation of the gear nut engages the external threads of the threaded post thereby coupling the superior plate to the inferior plate to form the expandable laminoplasty device. Rotation of the gear nut causes relative movement of the superior plate and inferior plate from contracted to expanded positions wherein stopping the rotation of the gear nut fixes an amount of linear expansion between the superior and inferior plates.

The threaded post preferably has helical threads and the gear nut has complimentary helical threads. The threaded post has a pair of flats extending along the length of the threaded post. The slot or channel is an oval opening with a pair of flat sides, the flat sides prevent rotation of the threaded post while allowing linear movement of the threaded post into or out of or within the slot or channel.

In some embodiments, the threaded post has a pair of ends, a first end rigidly fixed to the superior plate or inferior plate and a second end for entering the slot or channel and threadingly engaging the gear nut. In another embodiment, the threaded post has a first end with an opening for receiving a pin, the threaded post when affixed to the superior plate having a pair of openings to hold the pin allows the superior plate to pivot about the threaded post. In all these embodiments, rotational movement of the gear nut provides a continuous adjustment of the movement between the contracted position and the expanded position.

The superior plate has a hooked end configured to engage a cut lamina of a cervical vertebra. The hooked end has an internal surface with ridges to contact and engage the lamina. The superior plate has a pair of holes to receive fasteners to attach the superior plate to the cut lamina bone.

The inferior plate has an end configured to contact the bone of a cervical vertebra. The end of the inferior plate has an inner surface for contacting the bone, the inner surface having a plurality of ridges to contact the bone. The end of the inferior plate has a pair of holes for receiving fasteners to affix the inferior plate to the cervical bone.

In other embodiments, an expandable laminoplasty device has a superior plate, an inferior plate, a racked gear post having a plurality of gear teeth, the racked gear post affixed to one of the superior plate or the inferior plate, and a pinion gear. The pinion gear has a plurality of gear teeth configured to engage the gear teeth of the racked gear post. The pinion gear is held in one of the superior plate or inferior plate not affixed to the racked gear post, wherein the superior plate or inferior plate not affixed to the racked gear post has an end with a slot or channel to receive the racked gear post and a side opening to receive and hold the pinion gear. Rotation of the pinion gear engages the gear teeth of the racked gear post thereby coupling the superior plate to the inferior plate to form the expandable laminoplasty device. Rotation of the pinion gear causes relative movement of the superior plate and inferior plate from contracted to expanded positions wherein stopping the rotation of the pinion gear fixes an amount of linear expansion between the superior and inferior plates. The racked gear post has the plurality of gear teeth complimentary to the plurality of gear teeth of the pinion gear. The racked gear post is substantially rectangular or square in cross section with one racked side and three flat sides extending along the length of the racked gear post. The slot or channel is an opening with flat sides, the flat sides prevent rotation of the racked gear post while allowing linear movement of the racked gear post into or out of or within the slot or channel. The racked gear post has a pair of ends, a first end rigidly fixed to the superior plate or inferior plate and a second end for entering the slot or channel and engaging the pinion gear. The racked gear post has a first end with an opening for receiving a pin, the racked gear post when affixed to the superior plate having a pair of openings to hold the pin allows the superior plate to pivot about the racked gear post. Rotational movement of the pinion gear provides a continuous adjustment of the movement between the contracted position and the expanded position. The superior plate has a hooked end configured to engage a cut lamina of a cervical vertebra. The hooked end has an internal surface with ridges to contact and engage the lamina. The superior plate has a pair of holes to receive fasteners to attach the superior plate to the cut lamina bone. The inferior plate has an end configured to contact the bone of a cervical vertebra, wherein the end of the inferior plate has an inner surface for contacting the bone, the inner surface having a plurality of ridges to contact the bone. The inferior plate has a pair of holes for receiving fasteners to affix the inferior plate to the cervical bone.

In other embodiments, the assembly includes a second post spaced from the racked gear post, wherein the racked gear post has the gear teeth facing inwardly and the gear is positioned in an central location on one of either the superior plate or inferior plate to expand or contract the assembly. The second post has a rectangular or square cross section. The second post has four flat sides. The combination of the second post the racked gear post fit into the slot or opening of the inferior or superior plate and prevents rotation of the two plates while allowing linear movement by the rotation of the pinion gear.

The present invention allows for the following methods to perform a laminoplasty procedure.

A method of performing a laminoplasty comprises the steps of preparing a cervical vertebra by cutting through a lamina and partially cutting through the lamina at a spaced second location; providing an expandable laminoplasty device having: a superior plate; an inferior plate; a threaded post having external threads, the threaded post affixed to one of the superior plate or the inferior plate; a gear nut, the gear nut having internal threads configured to engage external threads of the threaded post, the gear nut being held in one of the superior plate or inferior plate not affixed to the threaded post, wherein the superior plate or inferior plate not affixed to the threaded post has an end with a slot or channel to receive the threaded post and a side opening to receive and hold the gear nut; and wherein the rotation of the gear nut engages the external threads of the threaded post thereby coupling the superior plate to the inferior plate to form the expandable laminoplasty device, rotation of the gear nut causes relative movement of the superior plate and inferior plate from contracted to expanded positions wherein stopping the rotation of the gear nut fixes an amount of linear expansion between the superior and inferior plates; positioning the expandable laminoplasty device in a contracted position on the vertebra with a hooked end of the superior plated on the cut lamina and the inferior plate on the lateral mass of the vertebra; fastening ends of both superior and inferior plates to the cut lamina and the lateral mass respectively using fasteners; and rotating the gear nut to expand the expandable laminoplasty device to a location enlarging a spinal canal opening of the vertebra completing the laminoplasty.

A method of performing a laminoplasty comprises the steps of preparing a cervical vertebra by cutting through a lamina and partially cutting through the lamina at a spaced second location; providing an expandable laminoplasty device having: a superior plate; an inferior plate; a racked gear post having a plurality of gear teeth, the racked gear post affixed to one of the superior plate or the inferior plate; a pinion gear, the pinion gear having a plurality of gear teeth configured to engage the gear teeth of the racked gear post, the pinion gear being held in one of the superior plate or inferior plate not affixed to the racked gear post, wherein the superior plate or inferior plate not affixed to the racked gear post has an end with a slot or channel to receive the racked gear post and a side opening to receive and hold the pinion gear; and wherein the rotation of the pinion gear engages the gear teeth of the racked gear post thereby coupling the superior plate to the inferior plate to form the expandable laminoplasty device, rotation of the pinion gear causes relative movement of the superior plate and inferior plate from contracted to expanded positions wherein stopping the rotation of the pinion gear fixes an amount of linear expansion between the superior and inferior plates; positioning the expandable laminoplasty device in a contracted position on the vertebra with a hooked end of the superior plated on the cut lamina and the inferior plate on the lateral mass of the vertebra; fastening ends of both superior and inferior plates to the cut lamina and the lateral mass respectively using fasteners; and rotating the gear nut to expand the expandable laminoplasty device to a location enlarging a spinal canal opening of the vertebra completing the laminoplasty.

BRIEF DESCRIPTION OF THE DRAWINGS

The invention will be described by way of example and with reference to the accompanying drawings in which.

DETAILED DESCRIPTION OF THE INVENTION

Figure 1:
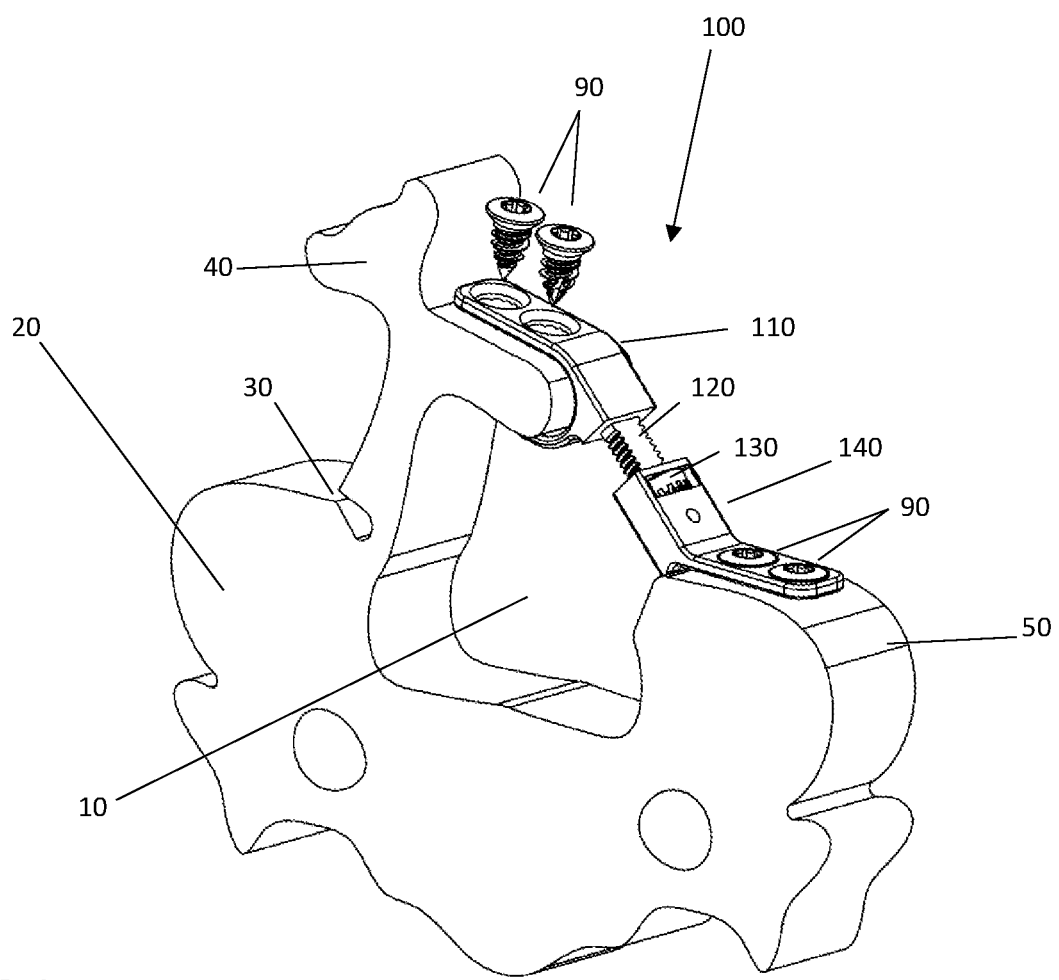
FIG. 1 is a perspective view of a first embodiment device of the present invention shown in an expanded position placed on an exemplary vertebra.

The following detailed description covers a variety of laminoplasty plates made in accordance with the present invention. It is important to note that the laminoplasty plates as illustrated in the FIGS. 1-43 represent alternative embodiments of the present invention that all employ a similar concept. That is the expandable laminoplasty device is a device having a superior plate with a J hook configuration which is designed to interface with the lamina of a vertebra of the spine, an inferior plate with a slight angle which is designed to interface with the lateral mass of the vertebra, and a threaded gear component which is designed to be housed in the superior or inferior plate having a threaded or geared interface with the opposite plate. One plate has a threaded or gear rack post that slides into the other plate and interfaces with a threaded gear or gear pinion component.

As illustrated in FIGS. 1-11, a first embodiment expandable laminoplasty plate 100 is shown wherein the threaded post 120 extends from a leading portion of the superior plate 110 and has a helical thread 122 that extends along two sides of the threaded post 120 and two opposing sides 124 that are machined flat configured to fit into a slot 145 of the inferior plate 140. The slot or channel 145 accepts the threaded post 120 which can slide freely into the slot 145 but is unable to rotate due to the flats 124 on the non-threaded portions or flats of the post. The threaded gear component 130 is a nut with a complimentary helical thread 132 that fits in an opening 148 of the inferior plate 140 allowing the threads 122 on the post 120 to be received and threadedly engaged. Rotation of the nut 130, when the post 120 is slipped into the opening 145 of the opposing plate, allows the nut 130 to be rotated such that the post 120 is driven inward into the plate 140 and when fully tightened is in a contracted position. The gear component or nut 130 has ridges or notches 131 to facilitate rotation.

Figure 2:
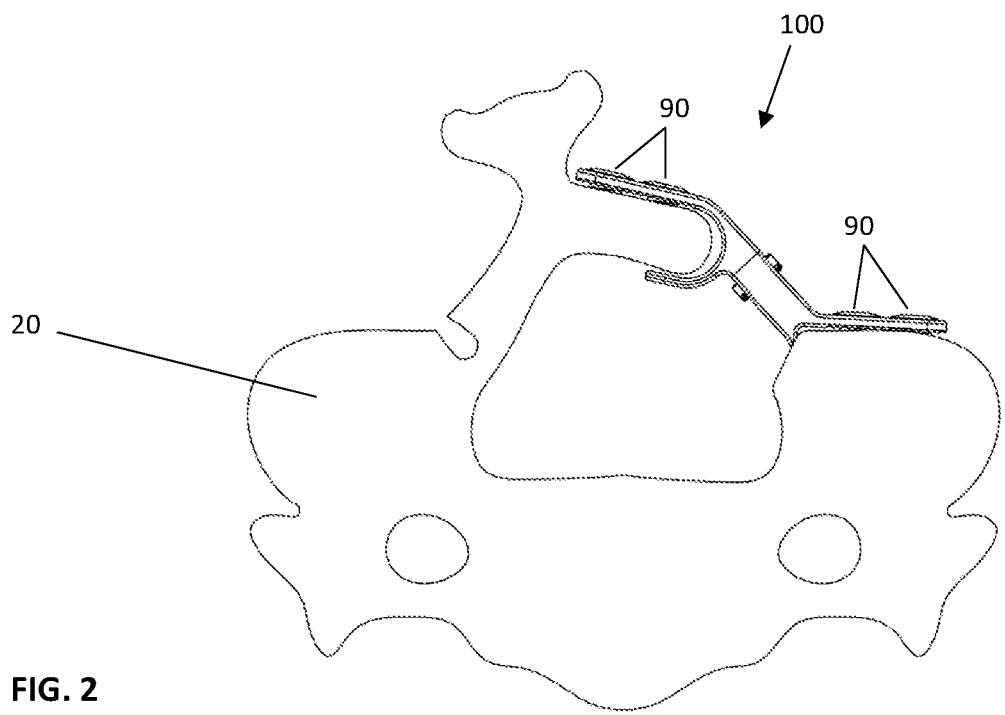
FIG. 2 is a side view of FIG. 1 showing the first embodiment device in a contracted position.
Figure 3:
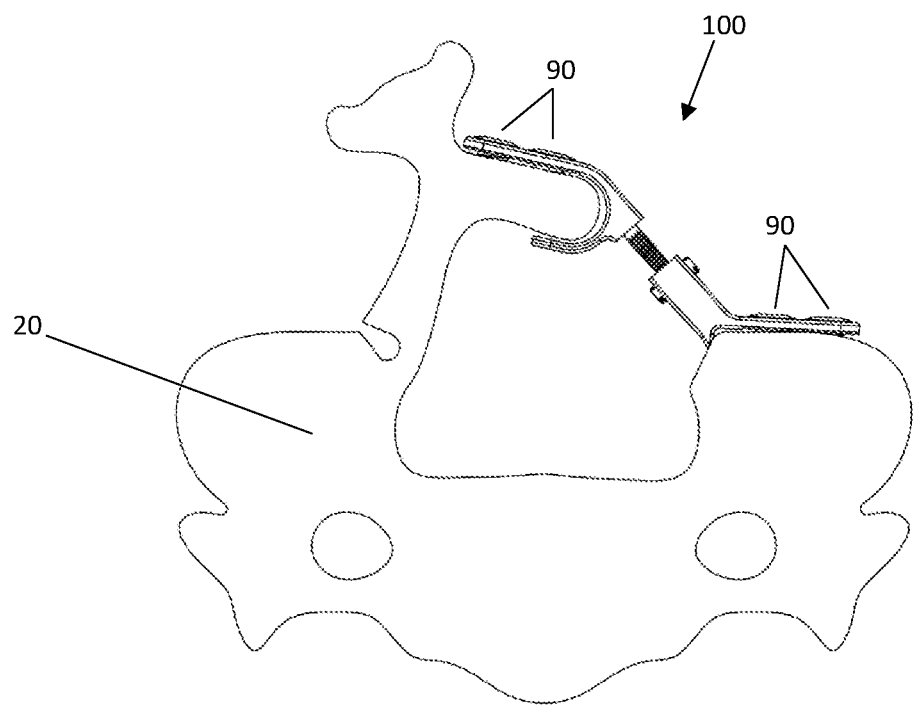
FIG. 3 is a side view of FIG. 1 showing the first embodiment device in an expanded position.

In FIG. 2, the first embodiment 100 is shown with the superior plate 110 engaging the lamina 40 and the inferior plate 140 engaging the lateral mass 50 in a contracted position. In FIG. 3, the device 100 is shown in an expanded position. These perspective and side views of FIGS. 1-3 allow one to visualize the large increase in the spinal canal 10 on this particular vertebra 20 and also shows the hinge point 30 of the lamina 40 where a partial cut 30 has been put in an opposite or outer side of the lamina such that when the expandable laminoplasty device 100 is expanded, it flexes against the hinged cut area 30 in the lamina and allows the opening in the spinal cord cavity 10 to be increased dramatically. Ideally, the surgeon will select the amount of increase he wants by adjusting the threaded gear component to the desired location that he wants the lamina 40 to be in the expanded position.

Figure 4:
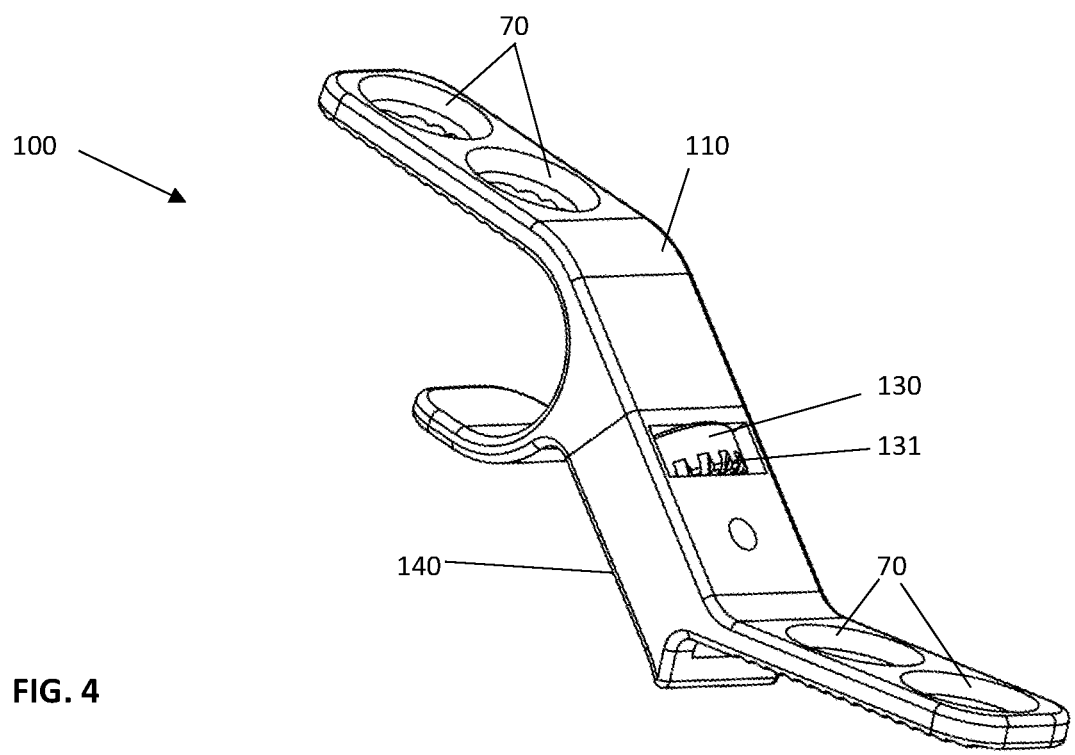
FIG. 4 is a front perspective view of the first embodiment contracted.
Figure 5:
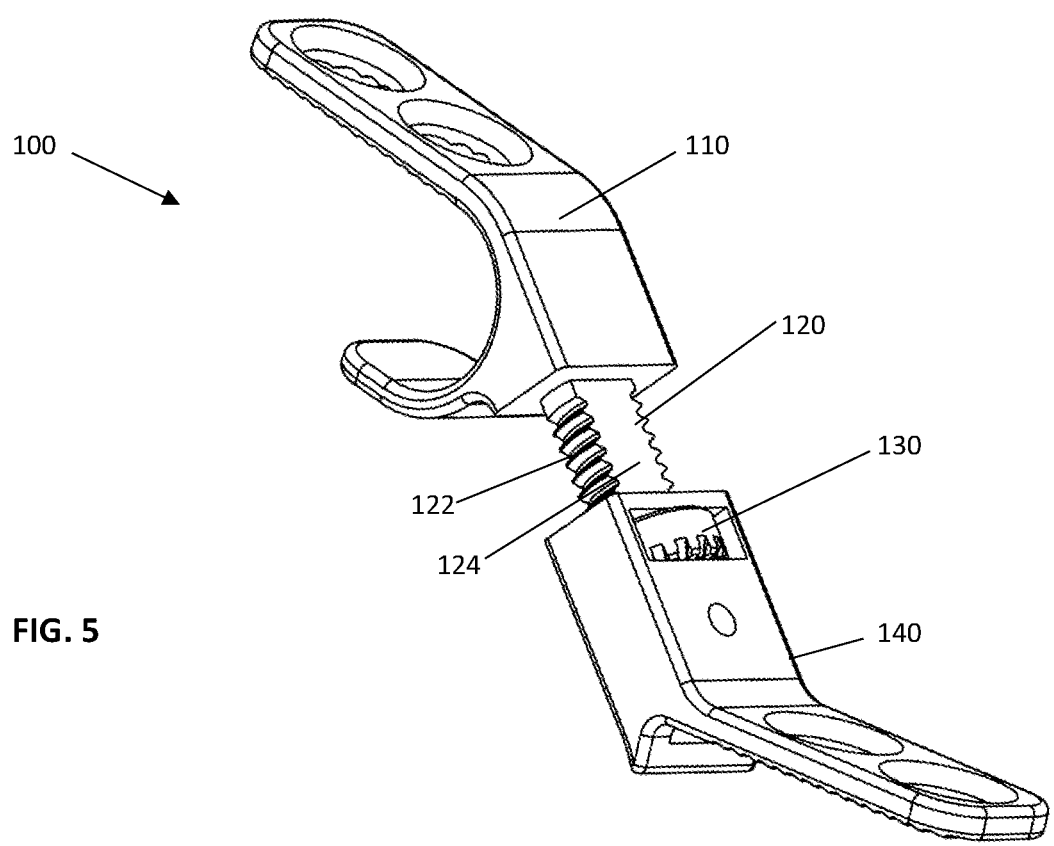
FIG. 5 is the front perspective view of the first embodiment expanded.

FIG. 4 shows the first embodiment expandable laminoplasty plate 100 in the contracted position. FIG. 5 shows the expandable laminoplasty plate 100 in a partially expanded position.

Figure 6:
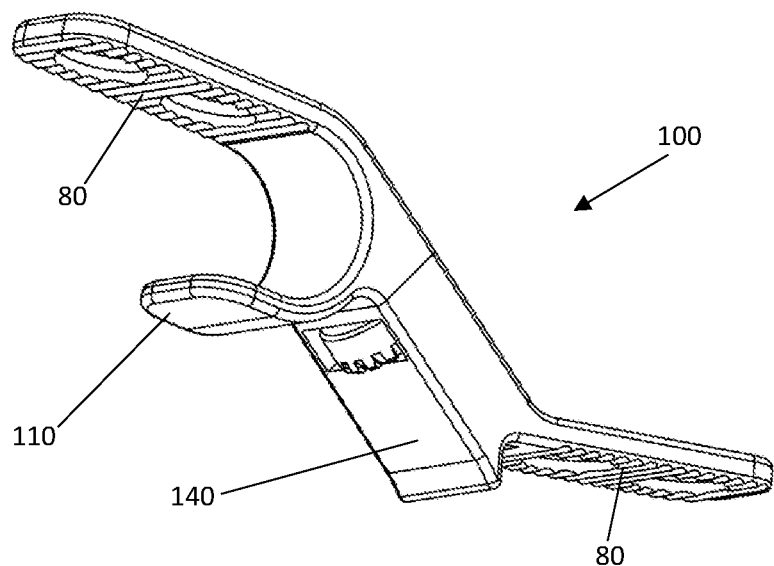
FIG. 6 is a bottom perspective view of the first embodiment contracted.
Figure 7:
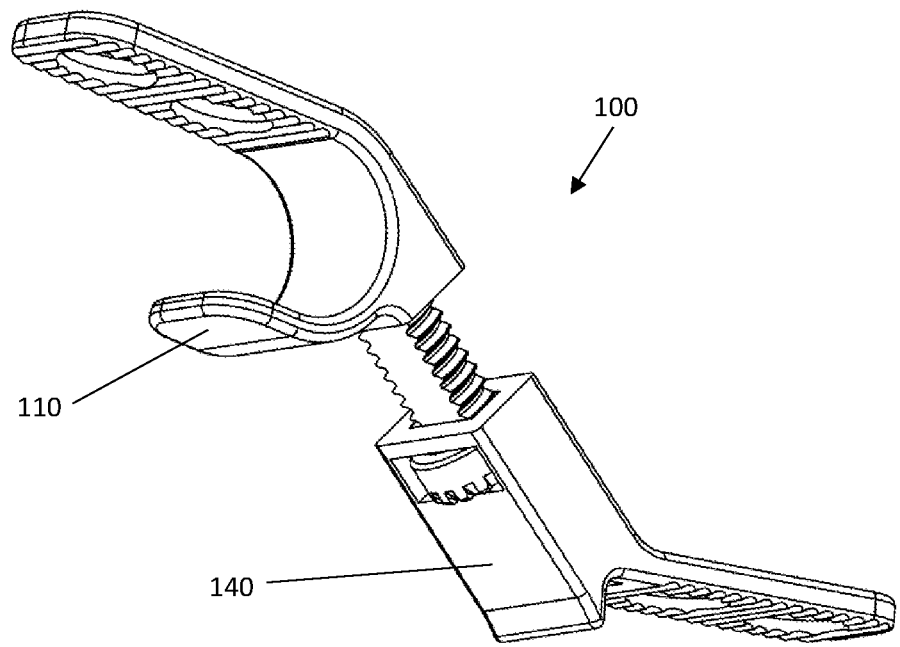
FIG. 7 is a bottom perspective view of the first embodiment expanded.

FIGS. 6 and 7 are perspective views showing the first embodiment laminoplasty plate 100 in contracted and expanded positions respectively. All of the illustrated embodiments have ridged or roughened surfaces 80, best shown in FIG. 6, on the superior and inferior plates for secure contact with the vertebra.

Figure 8:
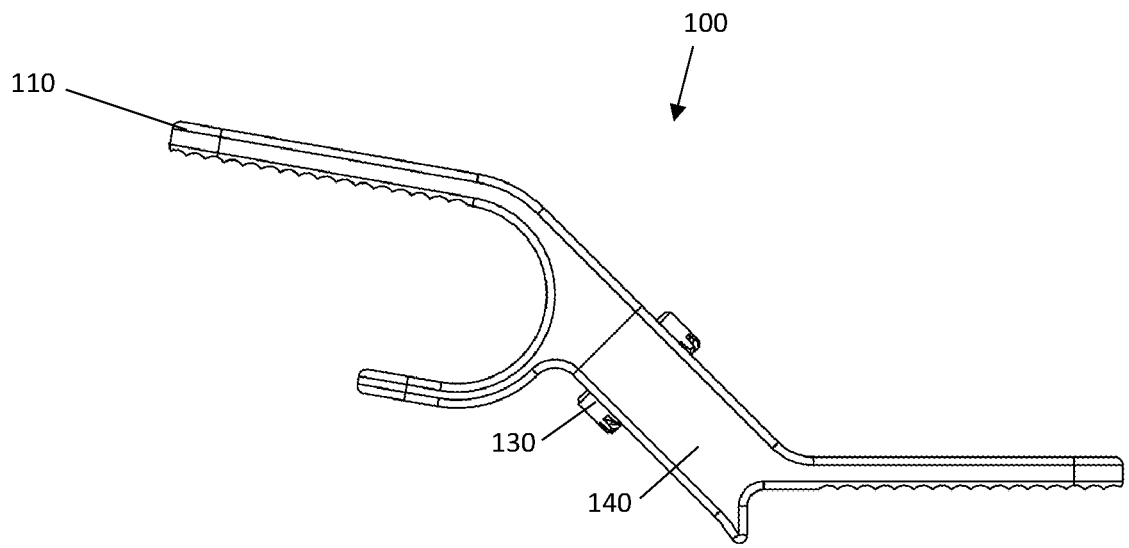
FIG. 8 is a side view of the first embodiment contracted.
Figure 9:
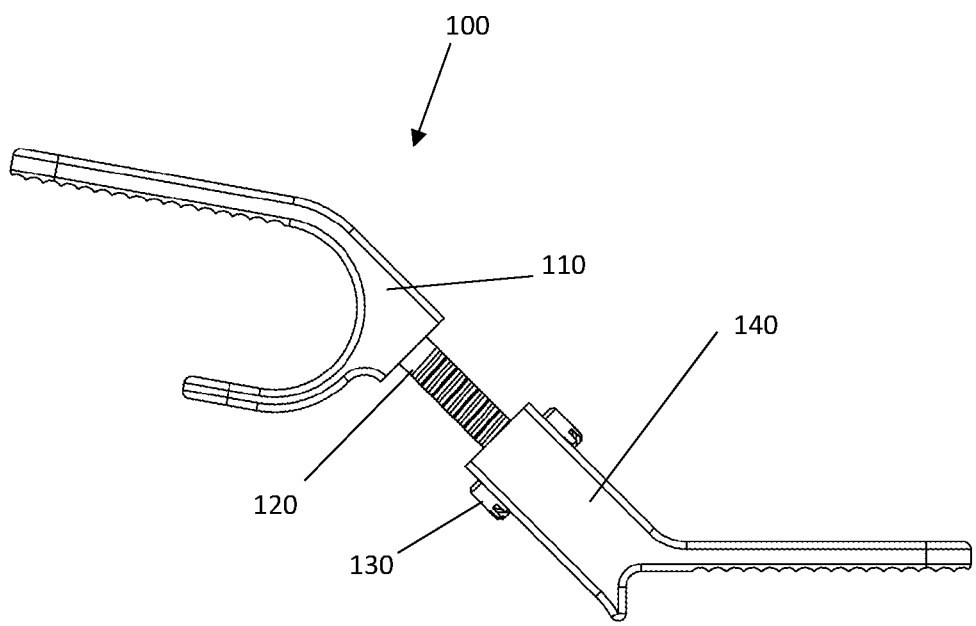
FIG. 9 is a side view of the first embodiment expanded.

FIGS. 8 and 9 are side views showing the first embodiment laminoplasty plate 100 in contracted and expanded positions respectively.

Figure 10:
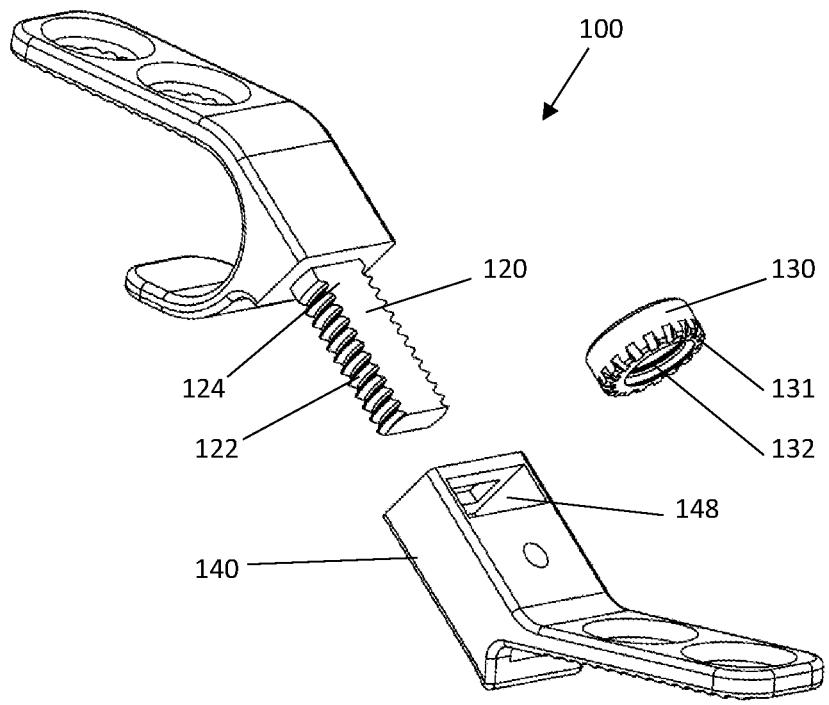
FIG. 10 is an exploded front perspective view of the first embodiment and component parts.
Figure 11:
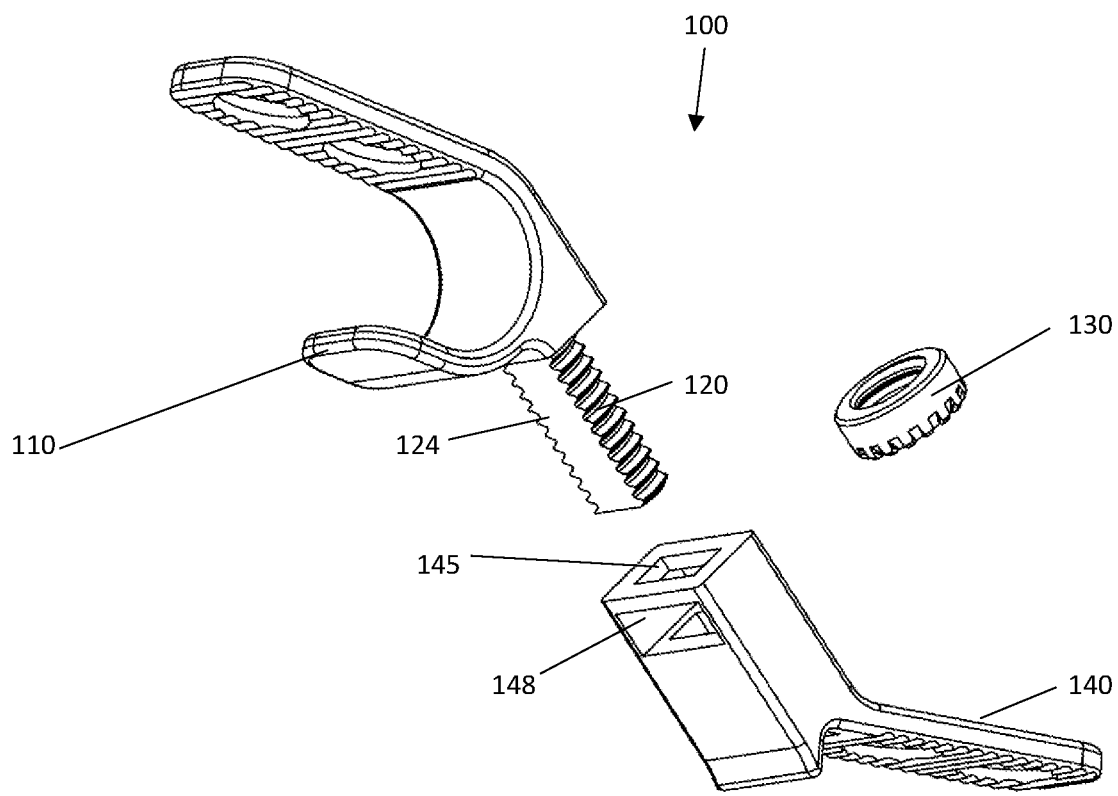
FIG. 11 is an exploded bottom perspective view of the first embodiment and component parts.

FIGS. 10 and 11 are exploded views of the first embodiment 100 showing the gear component 130, the superior plate 110 and inferior plate 140. The superior plate 110 having the threaded post 120 that slides into the inferior plate 140. The opening 145 at the top of the inferior plate 140 receives the threaded post 120 and the side opening 148 receives the gear component 130. When the gear component 130 is put into position, it can threadingly engage the threaded post 120 to adjust the superior plate 110 inward or outward of the inferior plate 140.

Figure 12:
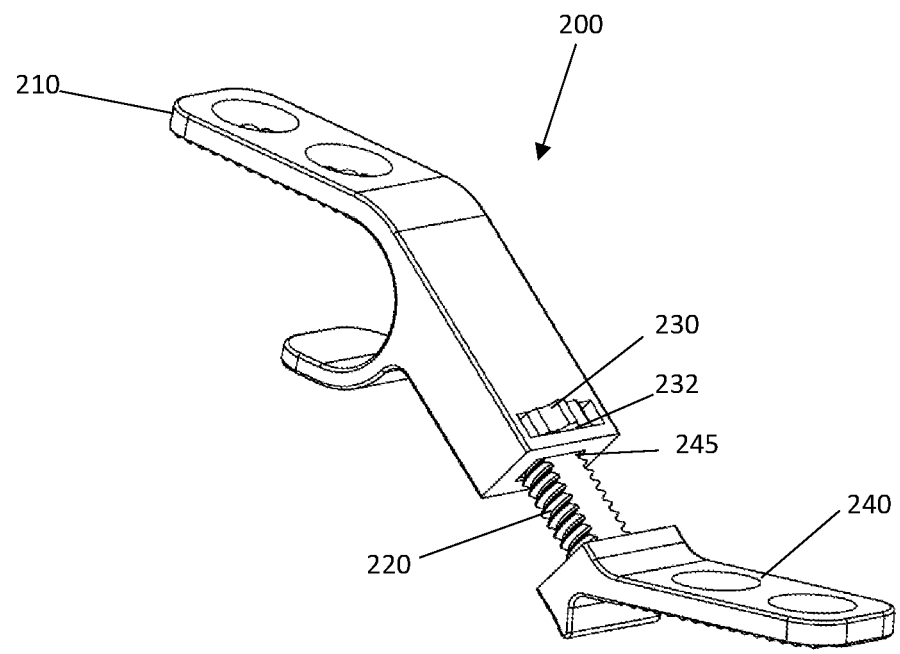
FIG. 12 is a front perspective view of a second embodiment of the present invention expanded.
Figure 13:
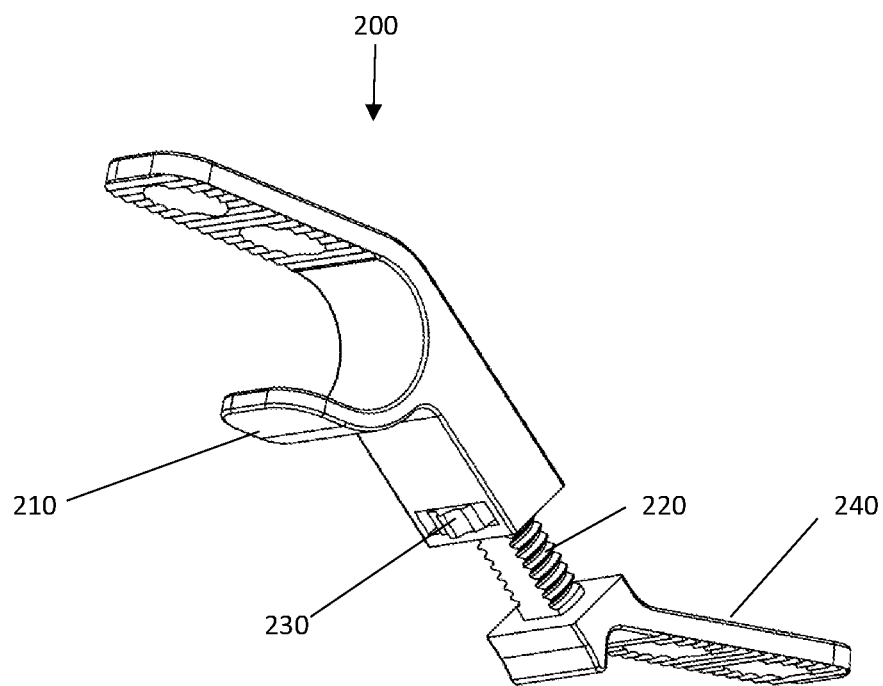
FIG. 13 is a bottom perspective view of the second embodiment expanded.
Figure 14:
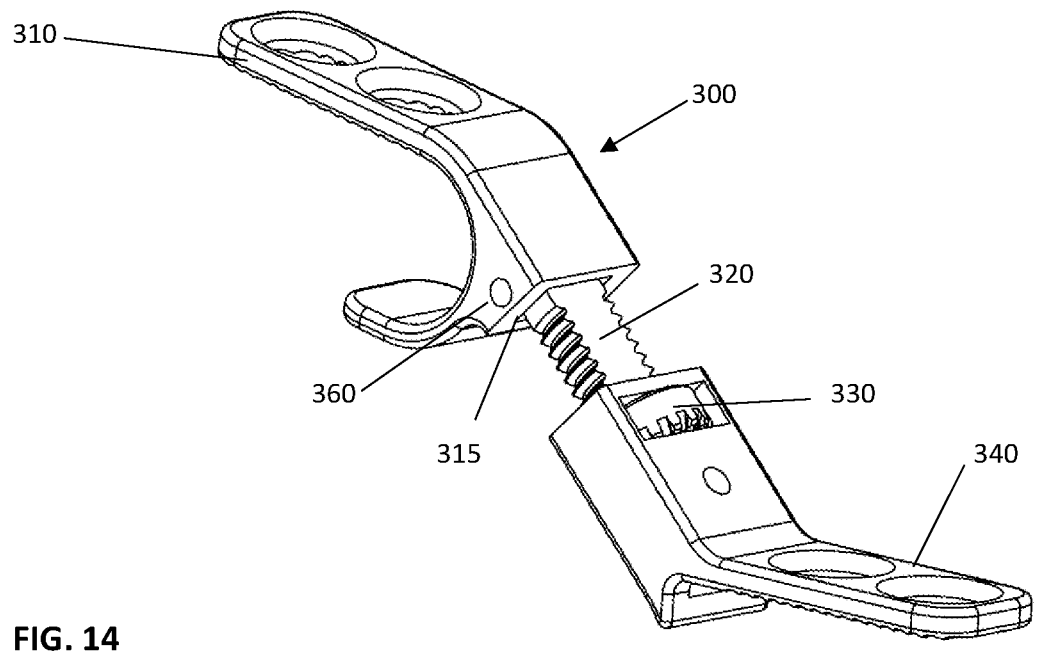
FIG. 14 is a front perspective view of a third embodiment of the present invention expanded.
Figure 15:
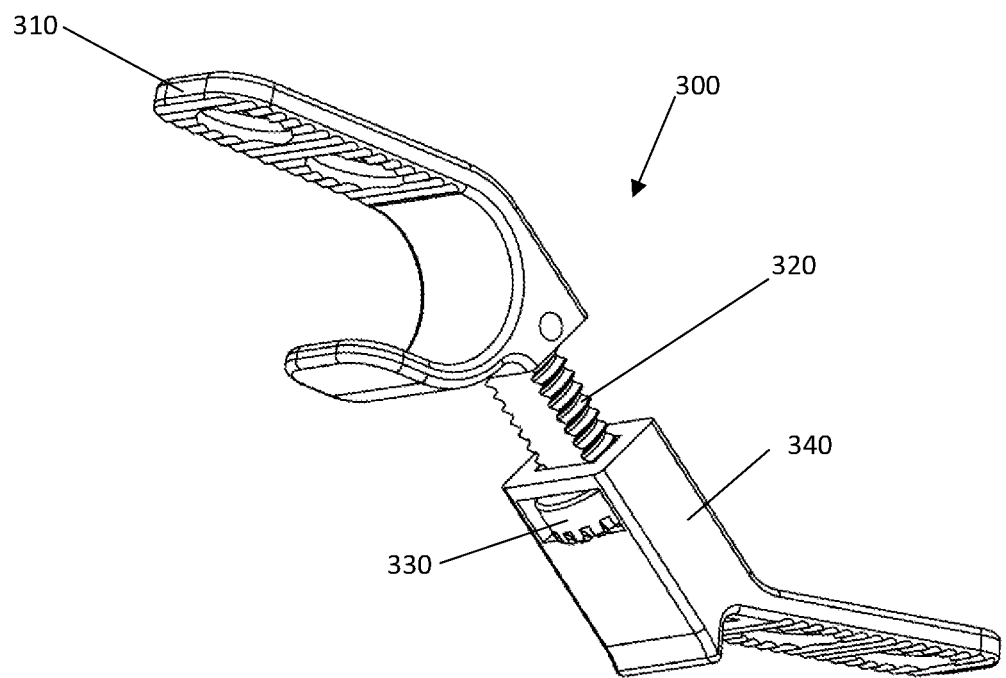
FIG. 15 is a bottom perspective view of the third embodiment expanded.

In an alternative second embodiment expandable laminoplasty device 200 shown in FIGS. 12 and 13, the post 220 is provided on the inferior plate 240 and the slotted channel 245 and gear component 230 are provided in the superior plate 210. In this configuration, the gear 230 engages the threaded post 220 to move the superior plate 210 to an expanded or contracted position relative to the inferior plate 240. This is simply using the same invention of the first embodiment, but alternating which plate receives the driving mechanism which is the threaded gear component and the threaded post.

Figure 16:
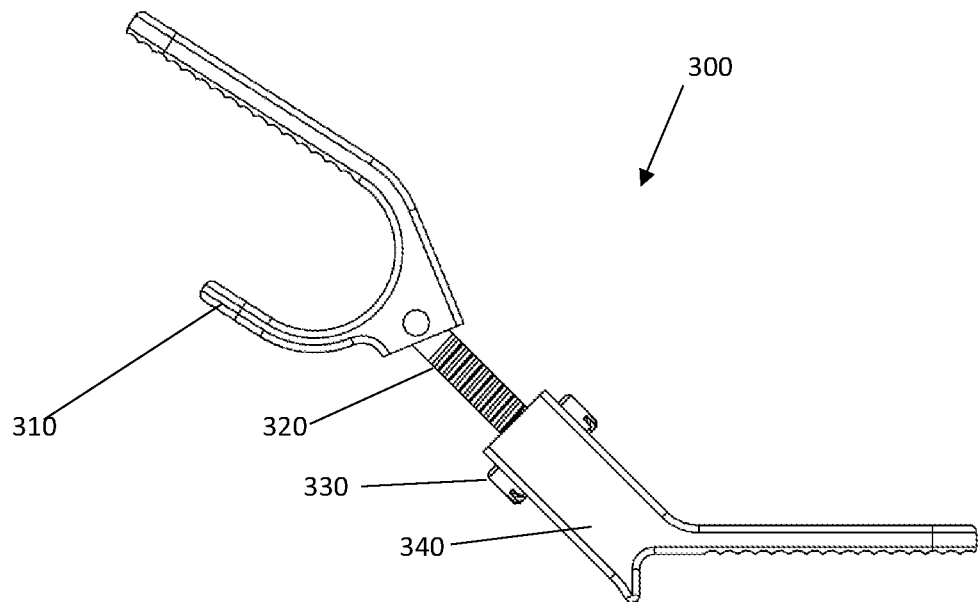
FIG. 16 is a side view of the third embodiment with superior plate facing upward.
Figure 17:
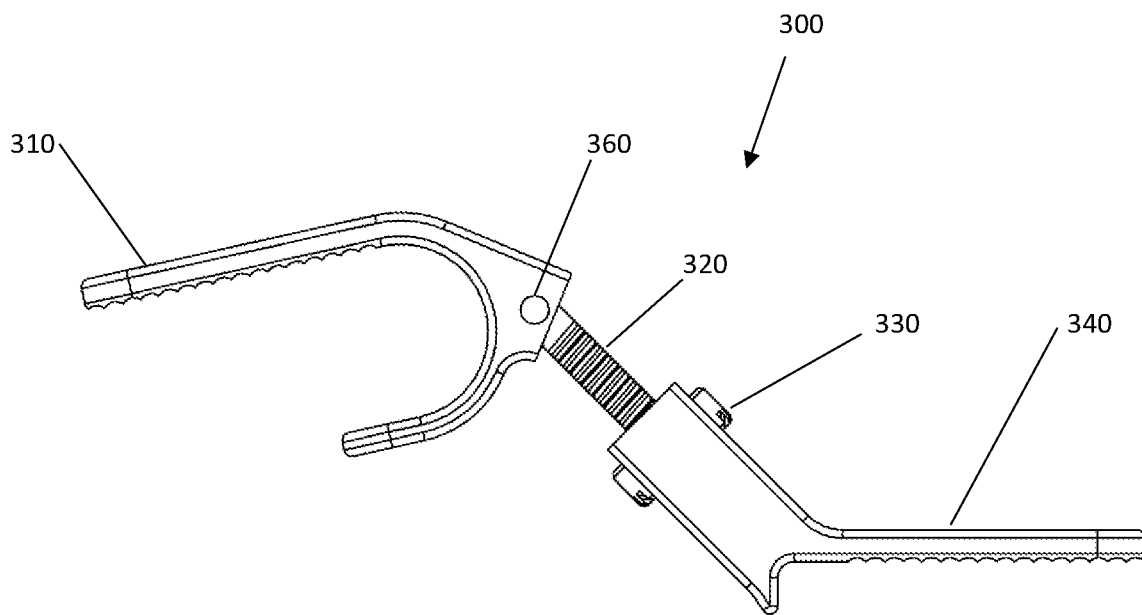
FIG. 17 is a side view of the third embodiment with superior plate facing downward.
Figure 18:
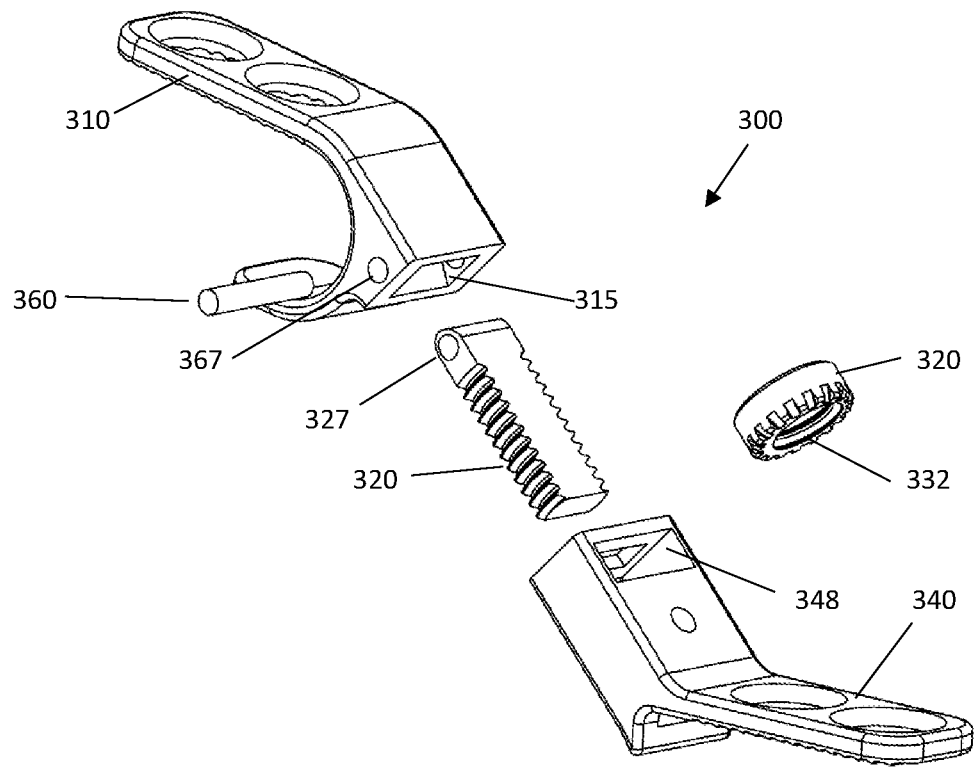
FIG. 18 is an exploded front perspective view of the third embodiment and component parts.
Figure 19:
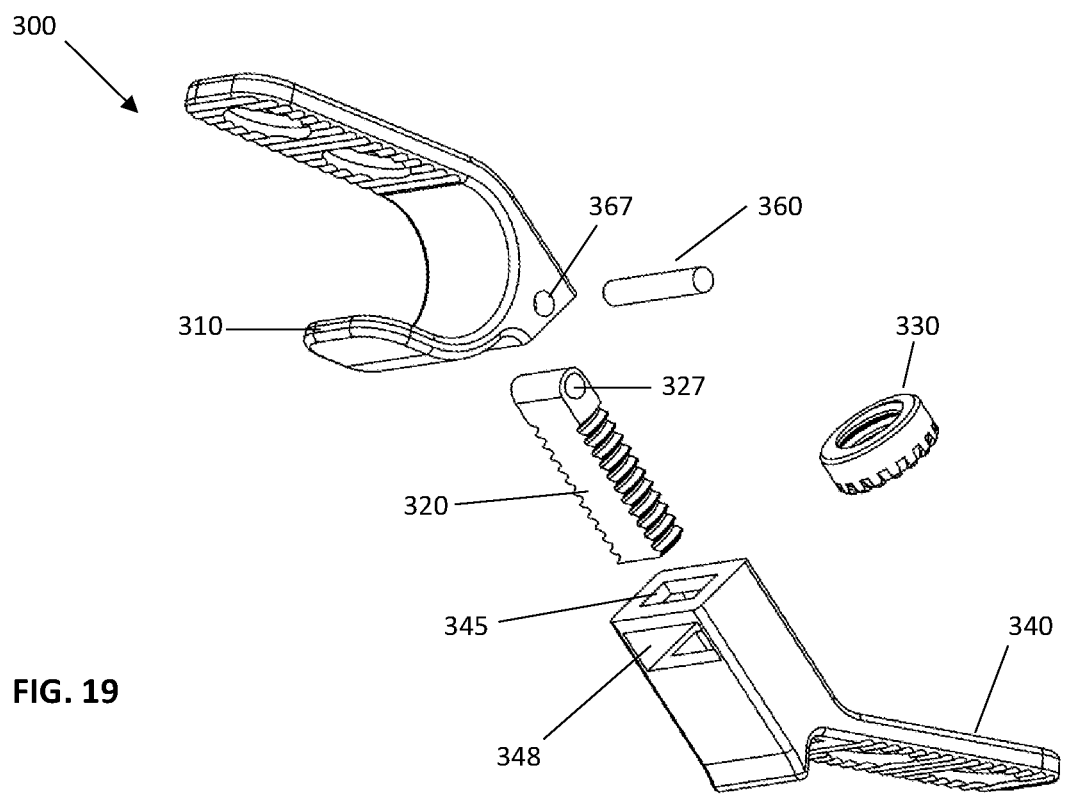
FIG. 19 is an exploded bottom perspective view of the third embodiment and component parts.

In a third embodiment expandable laminoplasty device 300 shown in FIGS. 14-19, similar to the first embodiment plate 100, the superior plate 310 has the threaded post 320 that extends to the inferior plate 340 which has the slot 345 and gear component 330 to expand and contract by moving the threaded post 320. However, in the third embodiment 300 a pivot pin 360 is provided at an end of the superior plate 310 with an opening slot 315 which receives the pin and is pinned to the threaded post 320. In this configuration, the superior plate 310 is able to pivot about the post 320 providing some angular flexibility in which to engage the lamina. This is best shown in FIGS. 16 and 17 side views. FIGS. 18 and 19 are exploded views of the third embodiment 300 showing how the threaded post 320 is pinned to the superior plate 310 illustrating the opening 327 in the threaded post 320 that receives the pin 360 that fits through a pair of openings 367 in the superior plate 310 which also has a slotted opening 315 to receive the superior end of the threaded post 320. Whereas the inferior end of the threaded post 320 fits into the slotted channel 345 of the inferior plate 340.

The threaded gear 130, 230, 330 with the internal helical thread 132, 232, 332 and the threaded post 120, 220, 320 of the first three embodiments 100-300 can be replaced with a rack and pinion system as shown in the following embodiments four through eight 400-800 of FIGS. 20-43. Various versions of this configuration are available using this similar concept. Again, the expansion and contraction of the superior plate relative to the inferior plate are all configured to be achieved by a rotation of a gear component.

In the fourth embodiment expandable laminoplasty device 400 FIGS. 20-27, the gear component 430 is a gear pinion shown on a side of the inferior plate 440 and the superior plate 410 has a racked gear post 420 with a plurality of gear teeth 422 extending outwardly to be received in a slotted channel 445 in the inferior plate 440.

Figure 20:
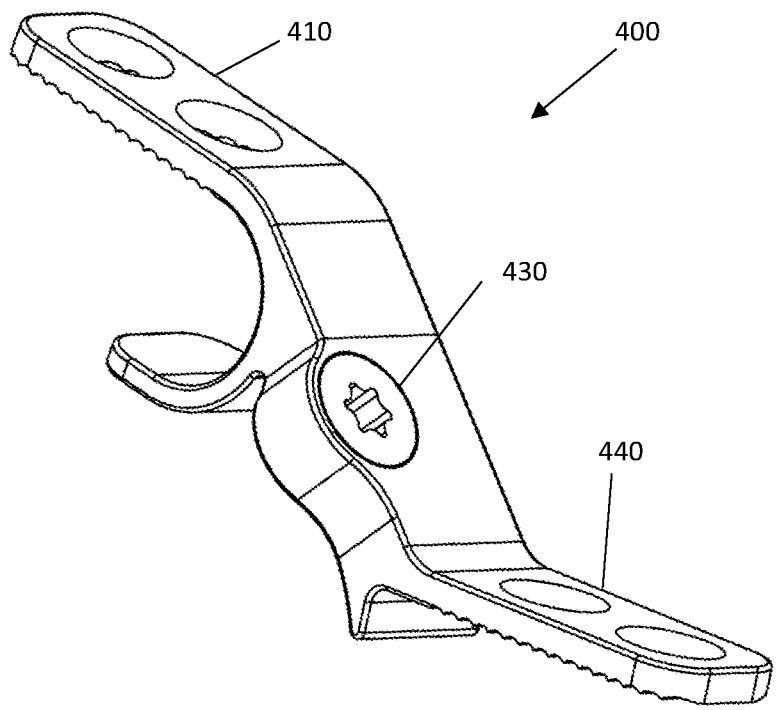
FIG. 20 is a front perspective view of a fourth embodiment of the present invention contracted.
Figure 21:
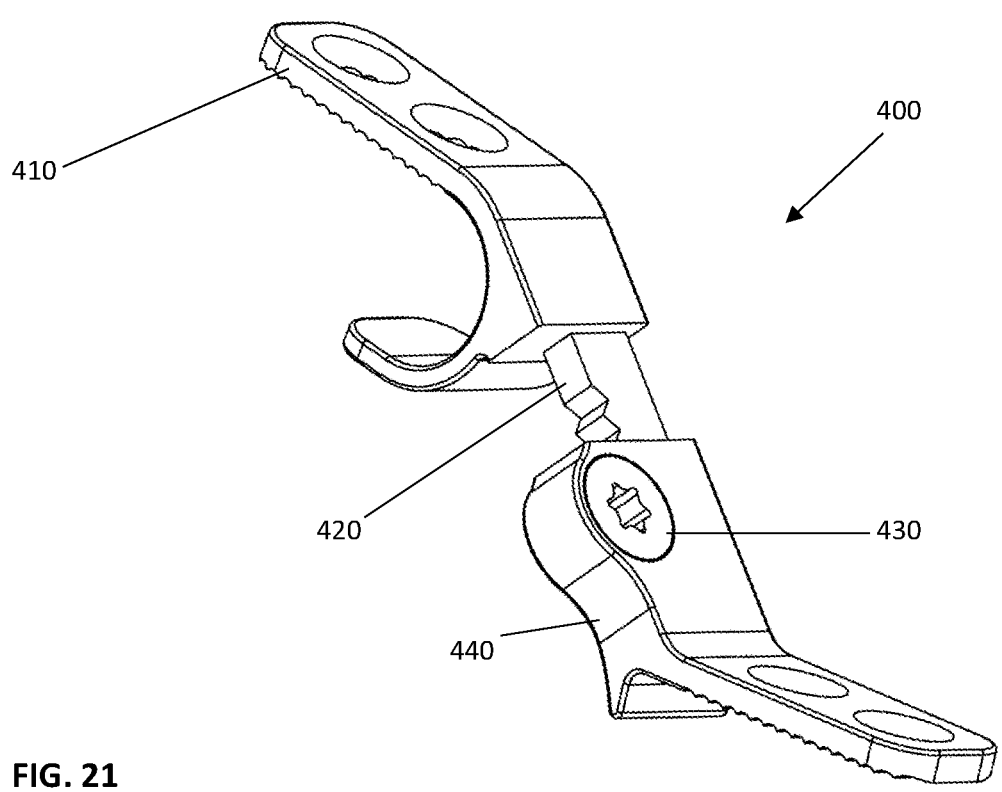
FIG. 21 is a front perspective view of the fourth embodiment expanded.
Figure 22:
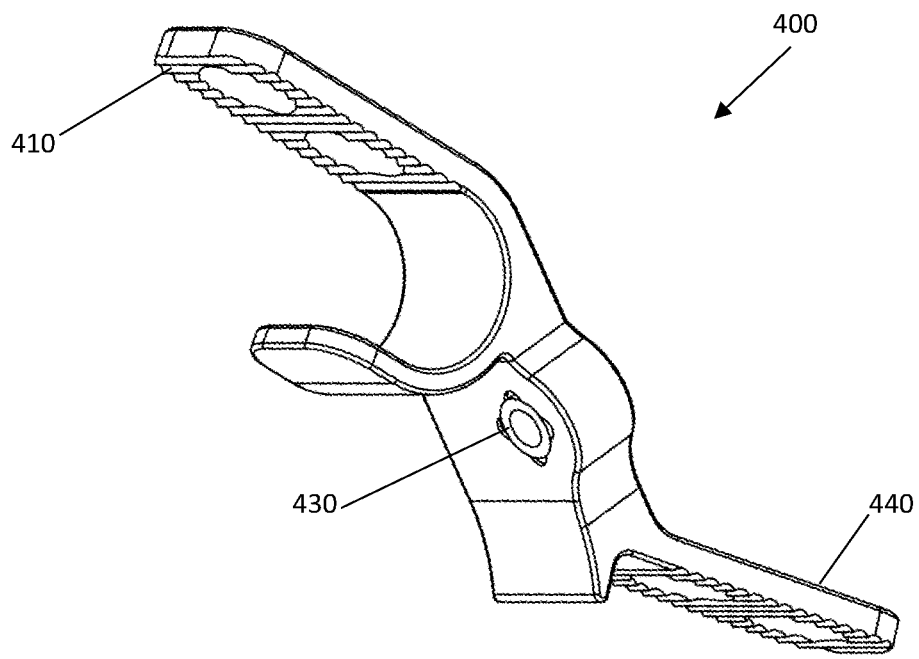
FIG. 22 is a bottom perspective view of the fourth embodiment contracted.
Figure 23:
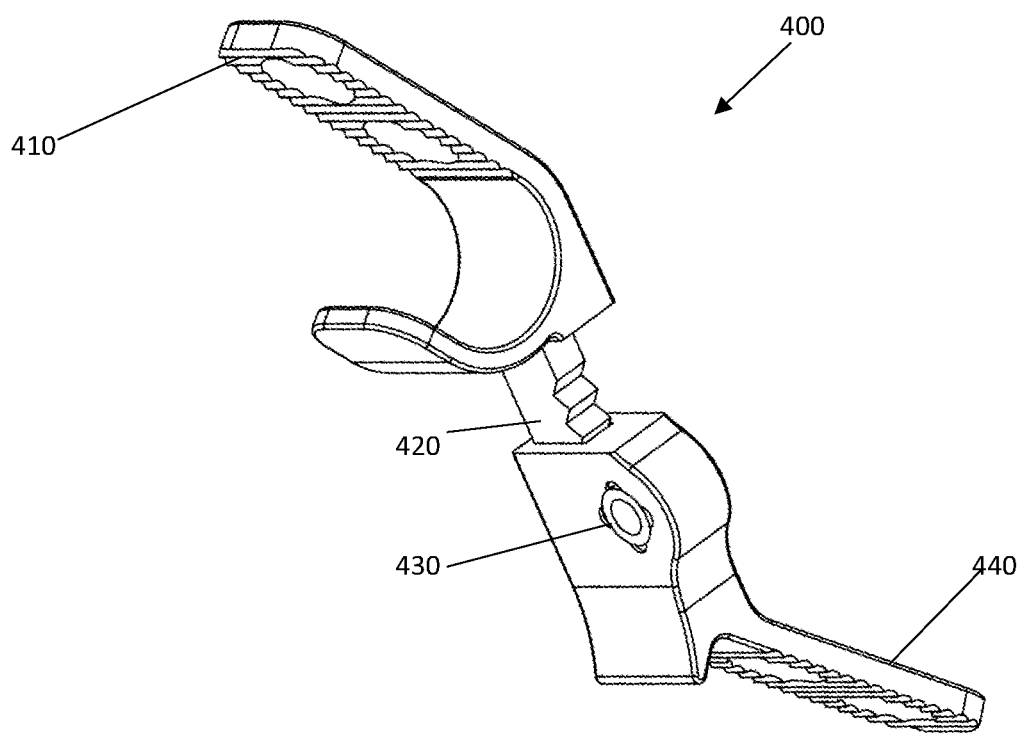
FIG. 23 is a bottom perspective view of the fourth embodiment expanded.
Figure 24:
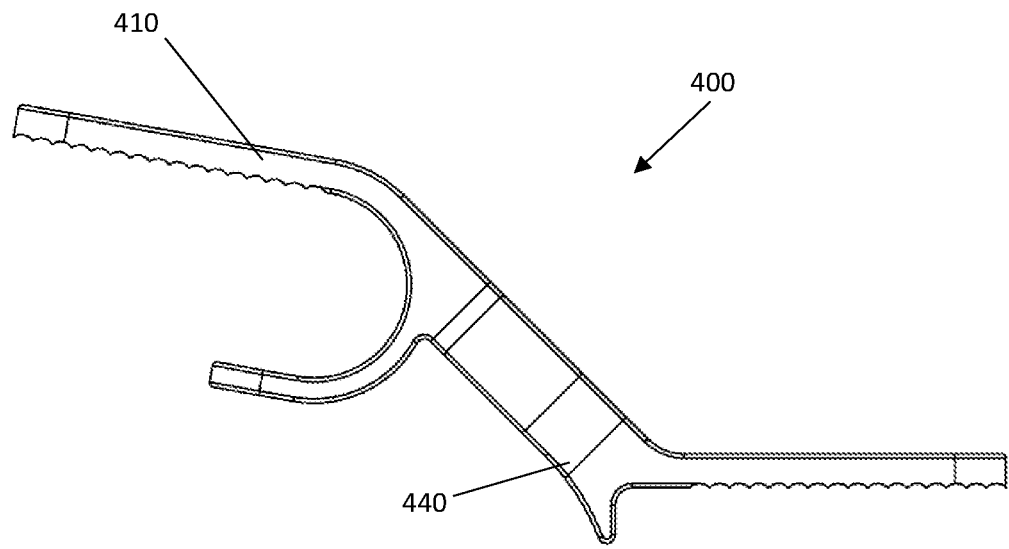
FIG. 24 is a side view of the fourth embodiment contracted.
Figure 25:
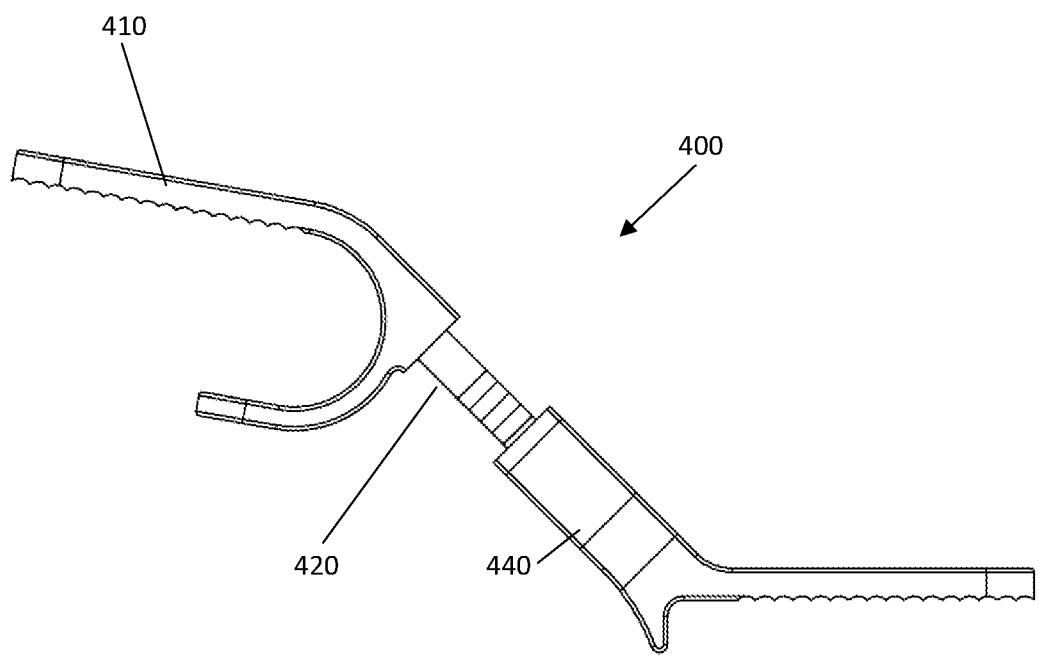
FIG. 25 is a side view of the fourth embodiment expanded.
Figure 26:
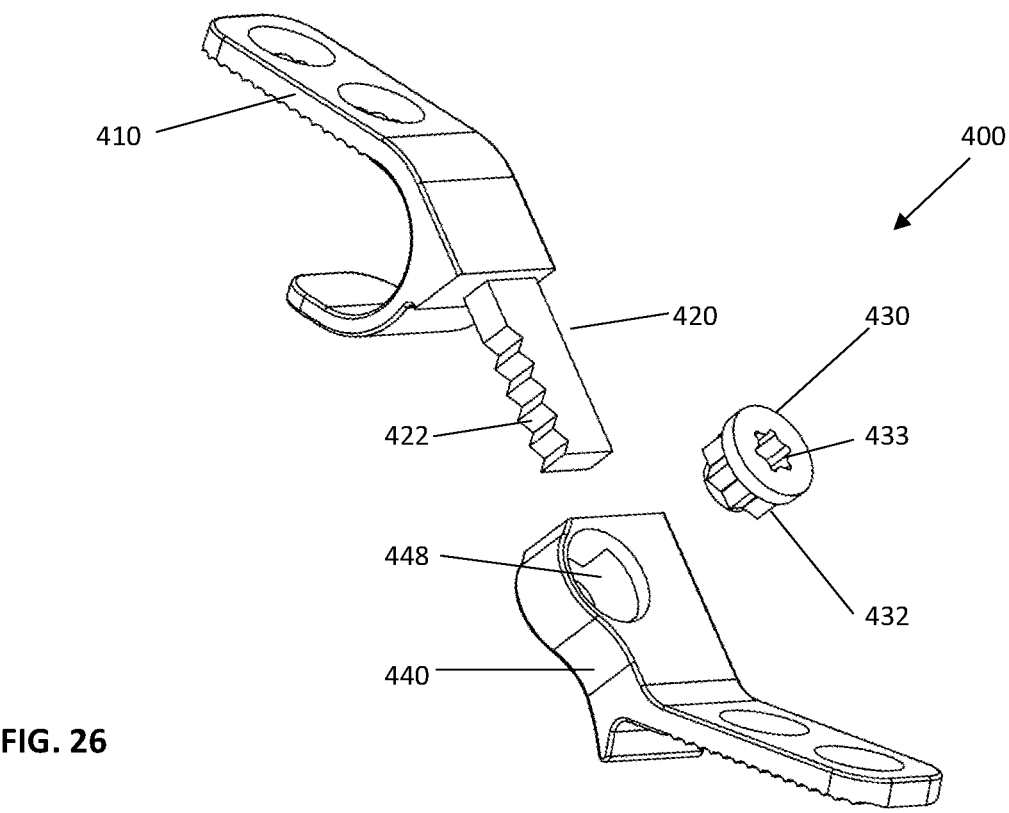
FIG. 26 is an exploded front perspective view of the fourth embodiment and component parts.
Figure 27:
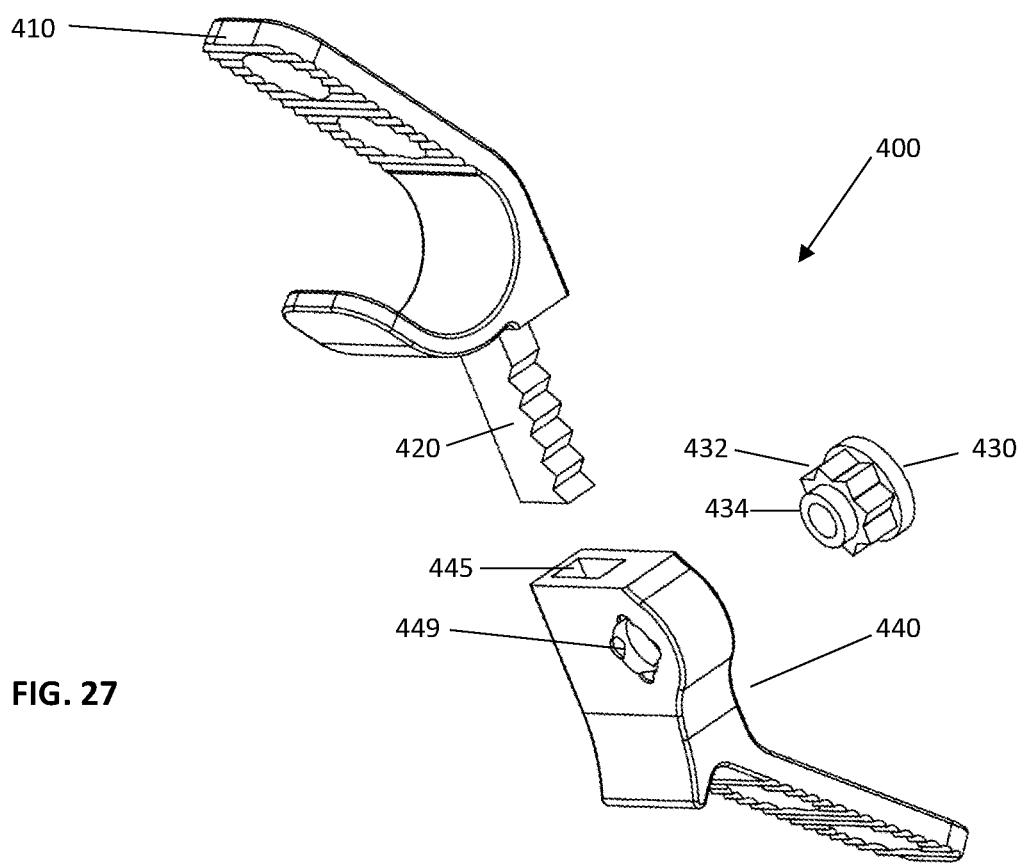
FIG. 27 is an exploded bottom perspective view of the fourth embodiment and component parts.

FIG. 20 shows the fourth embodiment assembly 400 in a contracted position. FIG. 21 shows the fourth embodiment assembly 400 in an expanded position. FIGS. 22 and 23 illustrate perspective views of the fourth embodiment assembly 400 contracted and expanded respectively. FIGS. 24 and 25 illustrate side views of the fourth embodiment assembly 400 contracted and expanded respectively. The exploded views of FIGS. 26 and 27 more clearly define the various components of the fourth embodiment assembly 400. As shown the racked gear post 420 and rotational gear component 430 similar to a rack and pinion in that the post 420 has the gear teeth 422 on one side of the post 420 and the gear 430 itself is pressed into, but free to rotate about the opening 448 in the inferior plate 440. As shown in FIG. 27 the gear 430 is swaged or pressed into the inferior plate 440 into the opening 448. The opening 448 has a plurality of recesses or cavities 449 that the protruding cylindrical portion 434 of the gear 430 is swaged or deformed into. When the recesses or cavities 449 of the opening 448 and the cylindrical portion 434 are swaged in the inferior portion 440 the gear pinion 430 is captively held there, but is able to be rotated to receive the superior plate 410 racked gear post 420.

Figure 28:
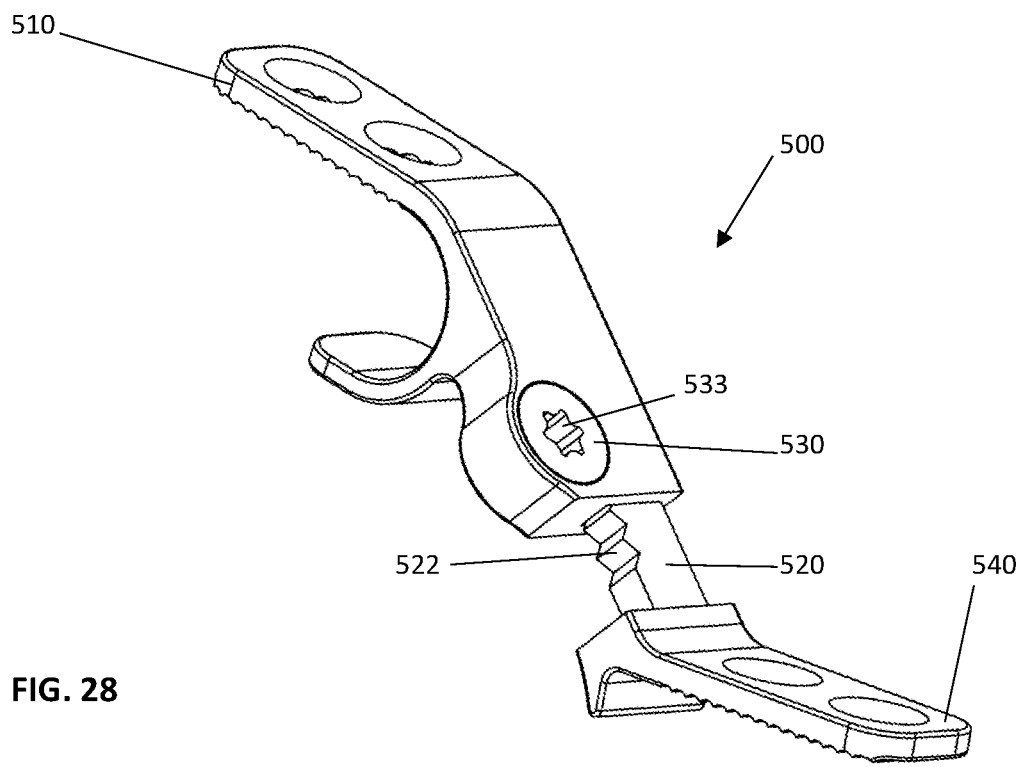
FIG. 28 is a front perspective view of a fifth embodiment of the present invention expanded.
Figure 29:
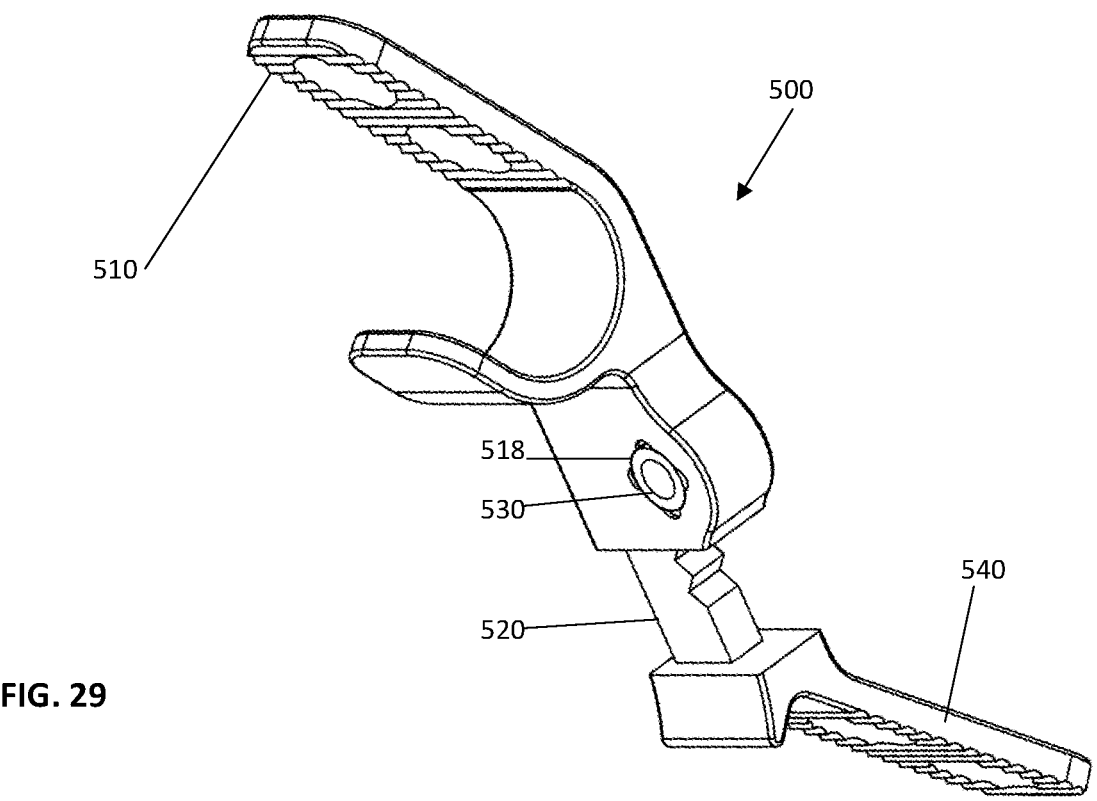
FIG. 29 is a bottom perspective view of the fifth embodiment expanded.
Figure 30:
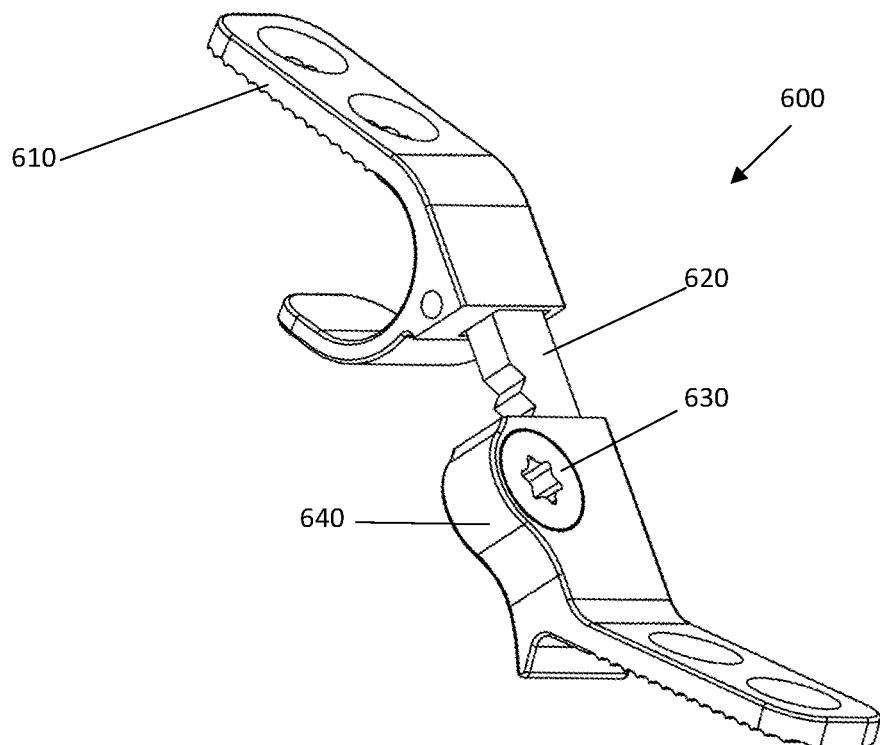
FIG. 30 is a front perspective view of a sixth embodiment of the present invention expanded.
Figure 31:
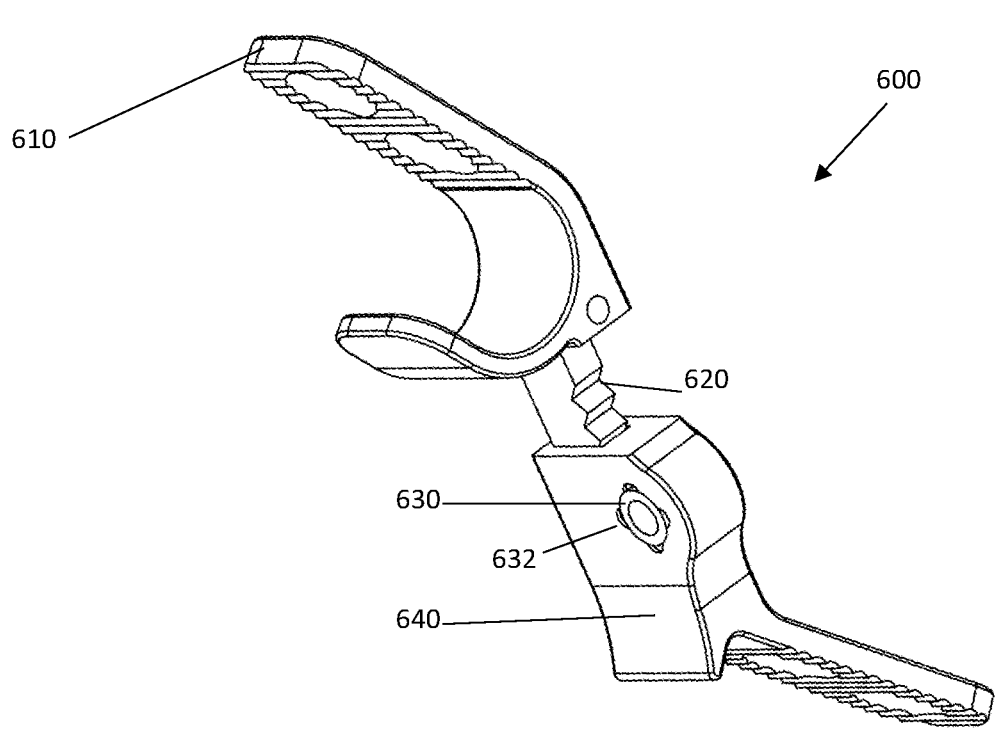
FIG. 31 is a bottom perspective view of the sixth embodiment expanded.
Figure 32:
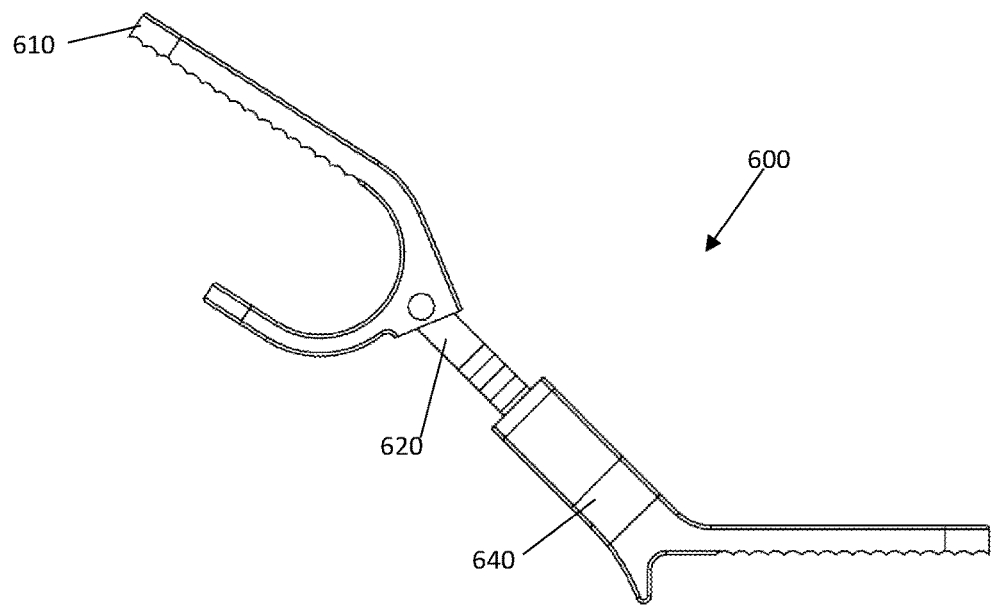
FIG. 32 is a side view of the sixth embodiment expanded with superior plate facing upward.
Figure 33:
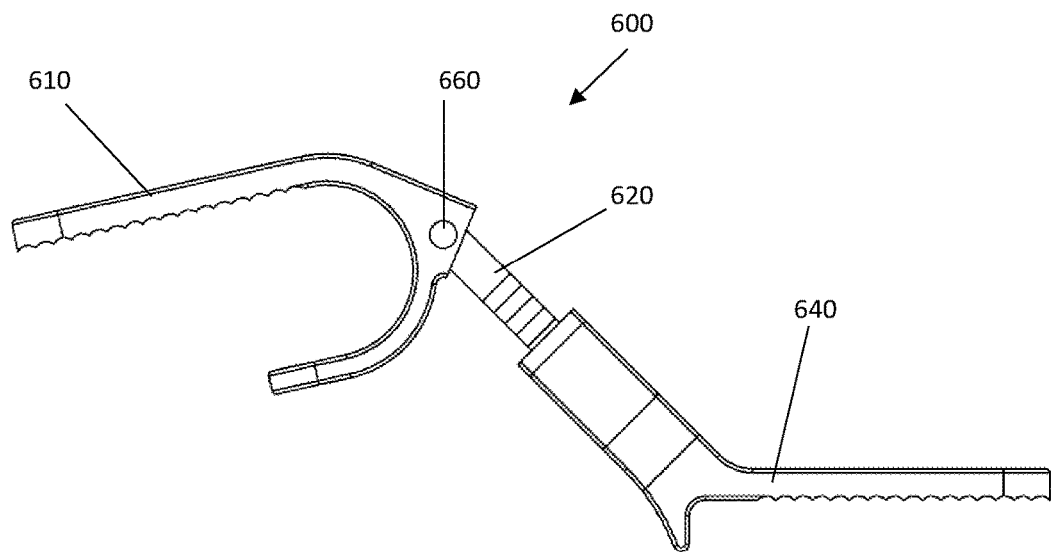
FIG. 33 is a side view of the sixth embodiment expanded with superior plate facing downward.
Figure 34:
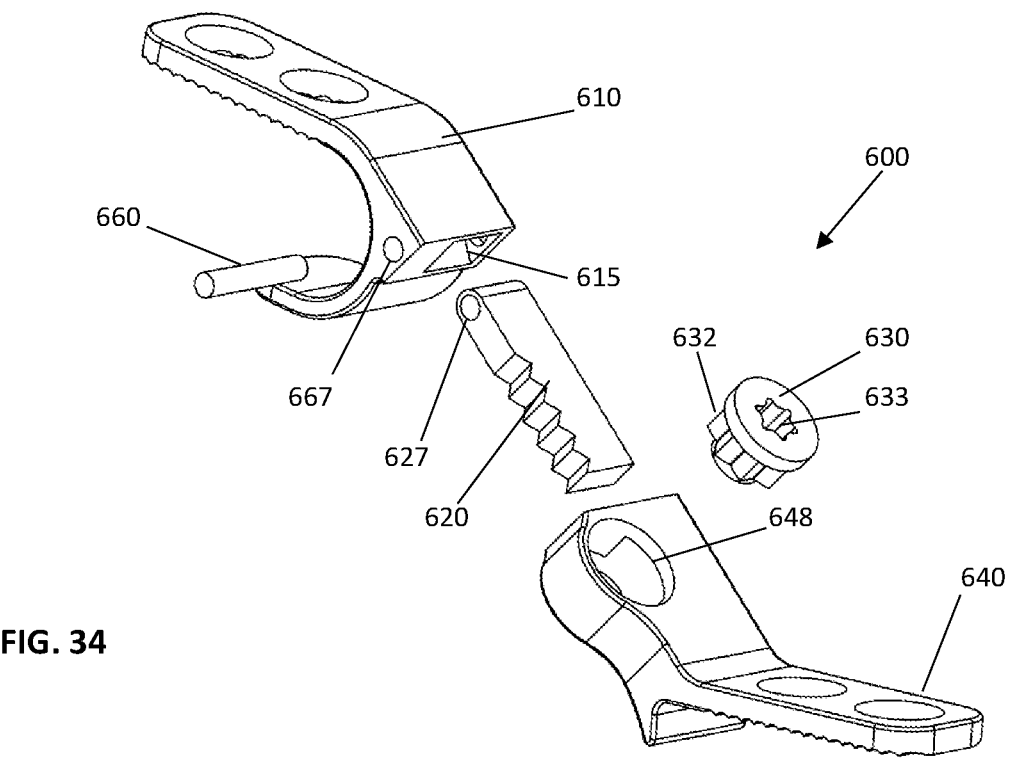
FIG. 34 is an exploded front perspective view of the sixth embodiment and component parts.
Figure 35:
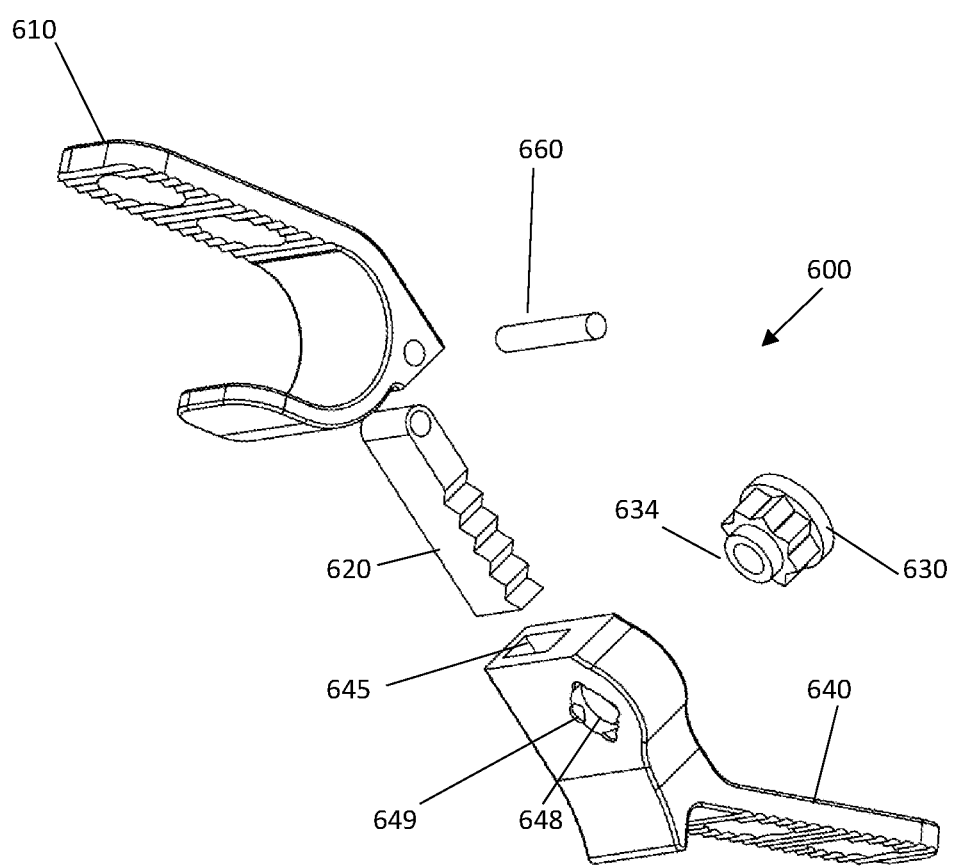
FIG. 35 is an exploded bottom perspective view of the sixth embodiment and component parts.
Figure 36:
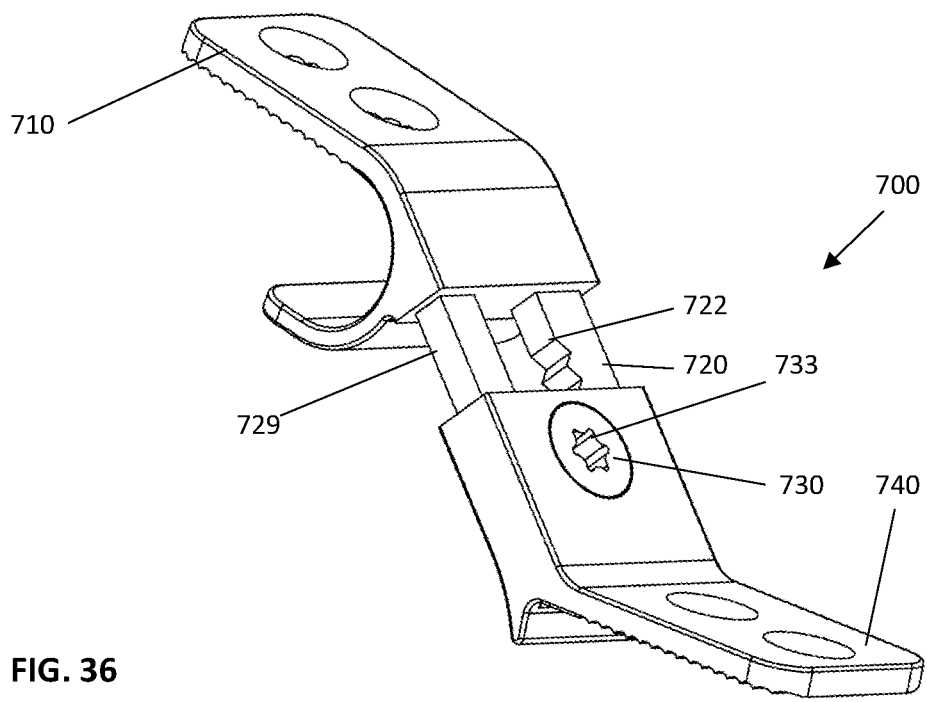
FIG. 36 is a front perspective view of a seventh embodiment of the present invention expanded.
Figure 37:
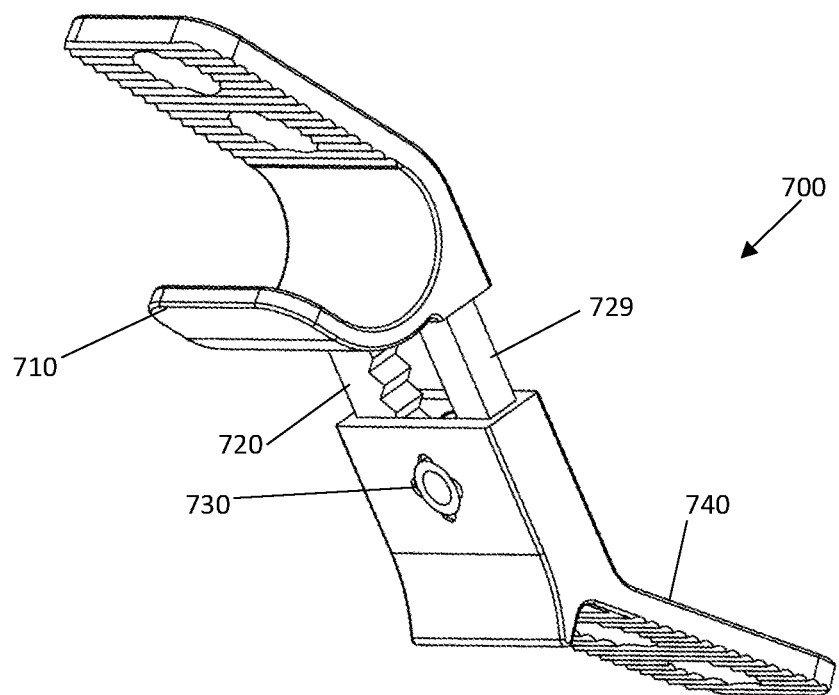
FIG. 37 is a bottom perspective view of the seventh embodiment expanded.
Figure 38:
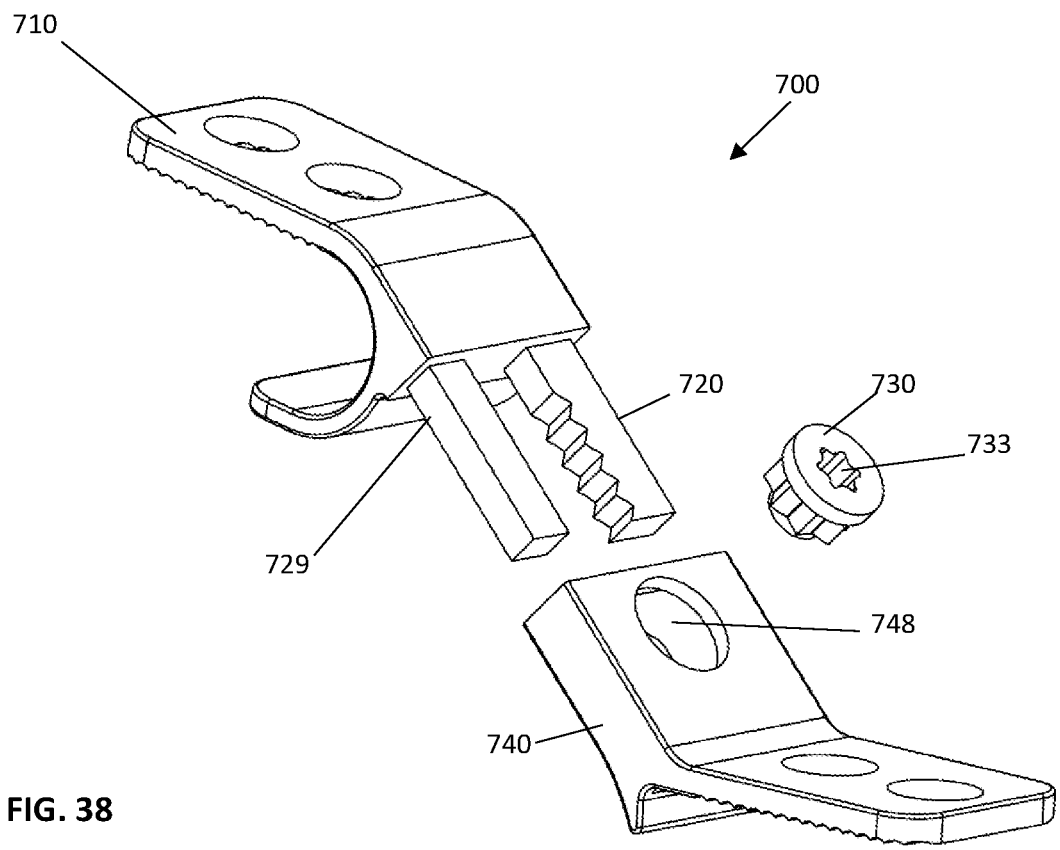
FIG. 38 is an exploded front perspective view of the seventh embodiment and component parts.
Figure 39:
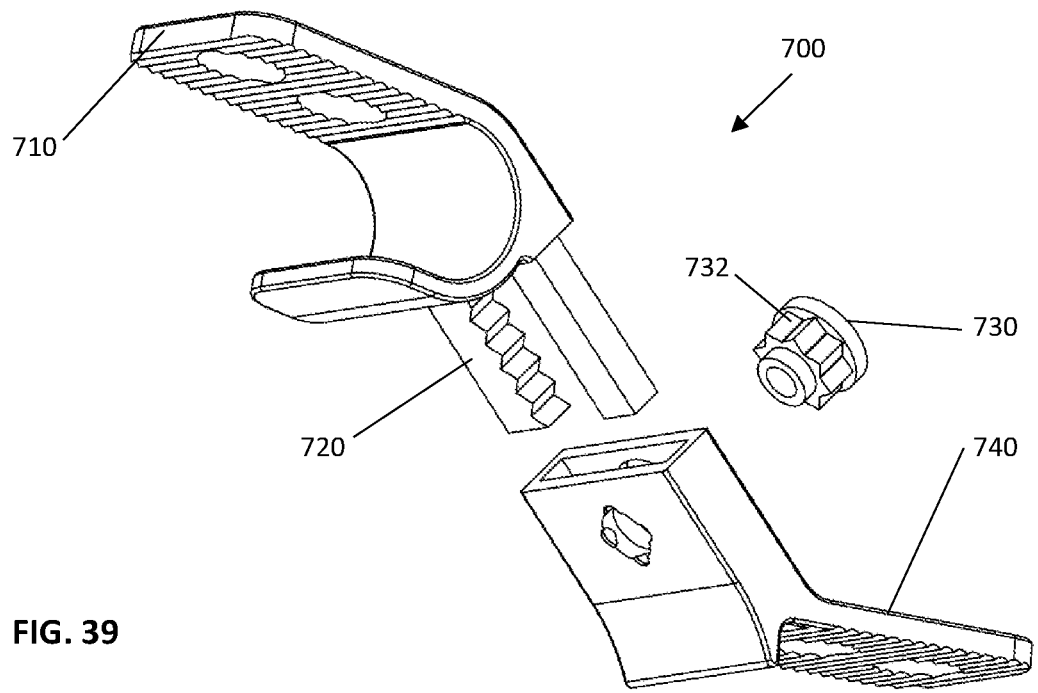
FIG. 39 is an exploded bottom perspective view of the seventh embodiment and component parts.
Figure 40:
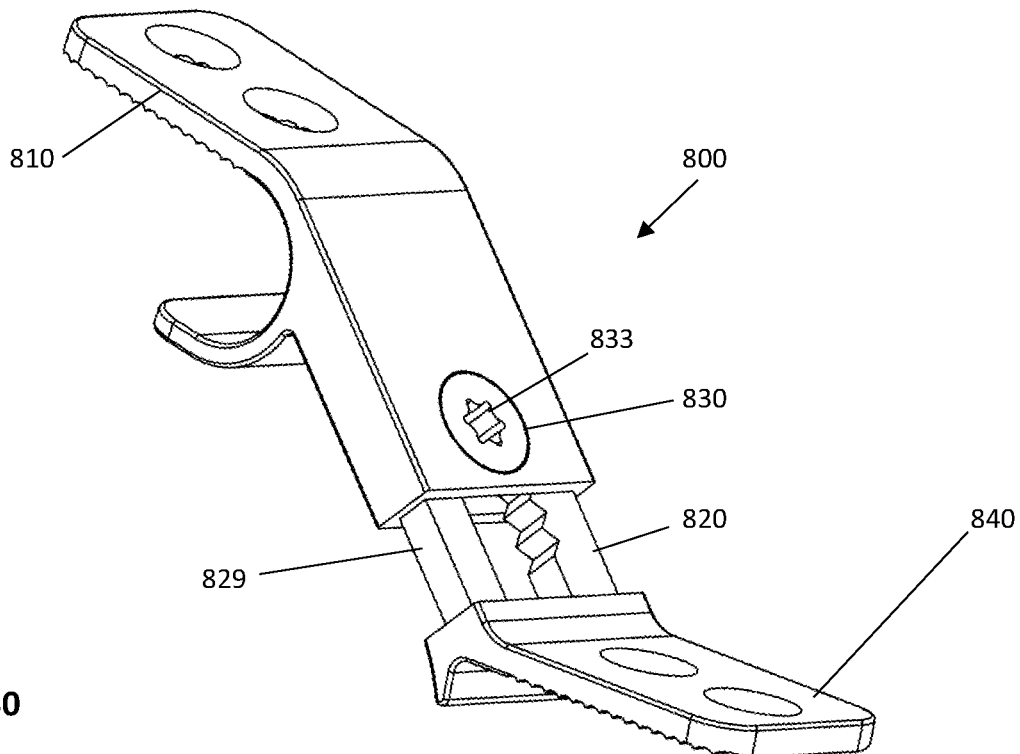
FIG. 40 is a front perspective view of an eighth embodiment of the present invention expanded.
Figure 41:
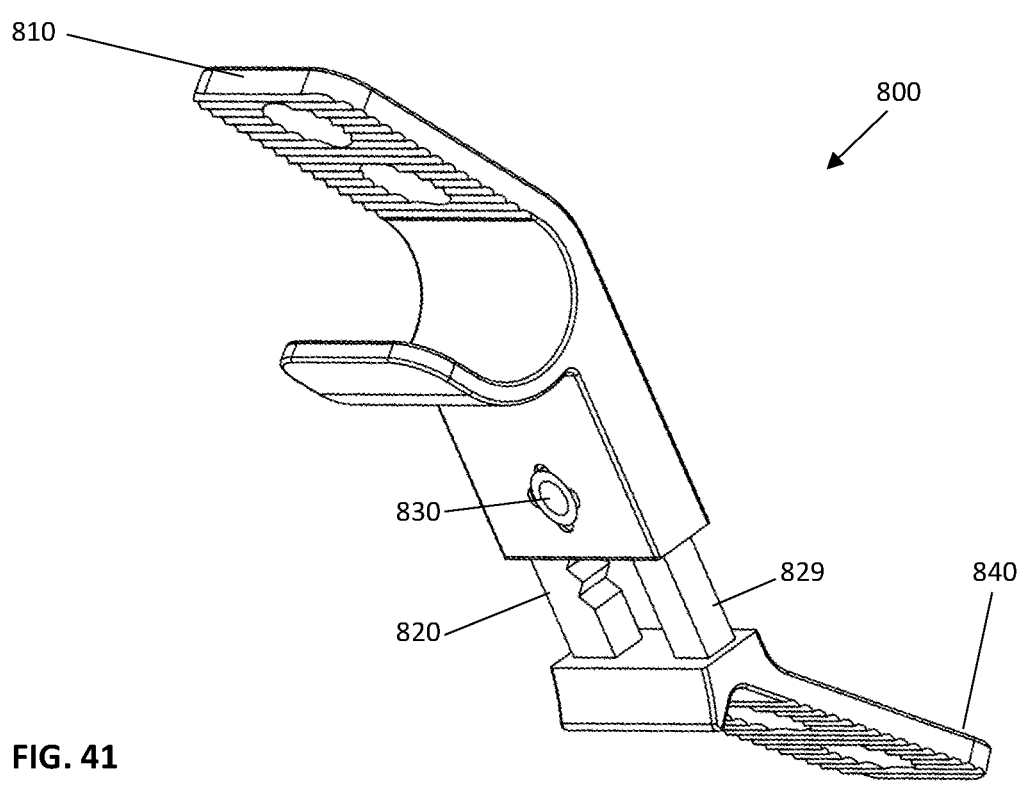
FIG. 41 is a bottom perspective view of the eighth embodiment expanded.

A fifth embodiment expandable laminoplasty device 500 is shown in FIGS. 28 and 29 wherein the racked gear post 520 is positioned on the inferior plate 540 and the rotational gear 530 is provided in the opening 518 of the superior plate 510. The fourth and fifth embodiment assemblies 400, 500 are identical other than which plate, inferior or superior, has the racked gear post 420, 520 or the rotational gear 430, 530.

In the embodiments 400-800 employing the racked gear post 420, 520, 620, 720 820, the gear component 430, 530, 630, 730, 830 has an opening 433, 533, 633, 733, 833 to receive a torqueing device, as shown, a star shaped opening so that the surgeon can turn and rotate the gear in such a fashion that it moves the superior plate and inferior plate in an expanded or contracted position relative to the other.

A sixth embodiment expandable laminoplasty device 600 of this invention is shown in FIGS. 30-35. Similar to the fourth embodiment 400, it has the racked gear post 620 on the superior portion 610. The sixth embodiment 600 also incorporates the pinning feature of the superior plate 610 similar to the third embodiment 300 which allows the superior plate 610 to pivot relative to the racked gear post 620 as previously discussed. This is best shown in the exploded views of FIGS. 34 and 35 wherein the pin 660 is shown near the superior plate 610. The superior plate 610 has a pair of openings 667 to receive the pin 660 that fits through an opening 627 in the racked gear post 620 to pivotally connect the superior plate 610 and the post 620. The racked gear post 620 fits into a slotted opening 615 of the superior plate 610 as illustrated. The inferior end of the gear post 620 fits into the slotted channel 645 of the inferior plate 640. Also similar to previous embodiments, the gear component 630 has a driver opening 633, gear teeth 632 and a cylindrical portion 634. The cylindrical portion 634 is held in place in the inferior plate 640 by the recesses or cavities 649 in the opening 648.

In a seventh embodiment expandable laminoplasty device 700 shown in FIGS. 36-39, the racked gear post 720 is configured slightly differently than the previous embodiments having a pair of posts 720, 729 extending from the superior plate 710. The gear mechanism 730 is positioned centrally on the inferior plate 740 in opening 748 and the pair of posts 720, 729 are positioned one on each side. Only one of the posts 720 has gear teeth 722 on one side. This enables the gear 730 with gear teeth 732 when turned to be able to drive the superior plate 710 in an expanded or contracted position as required. This provides a wider base and is a very stable configuration as an alternative to the single post configuration.

Figure 42:
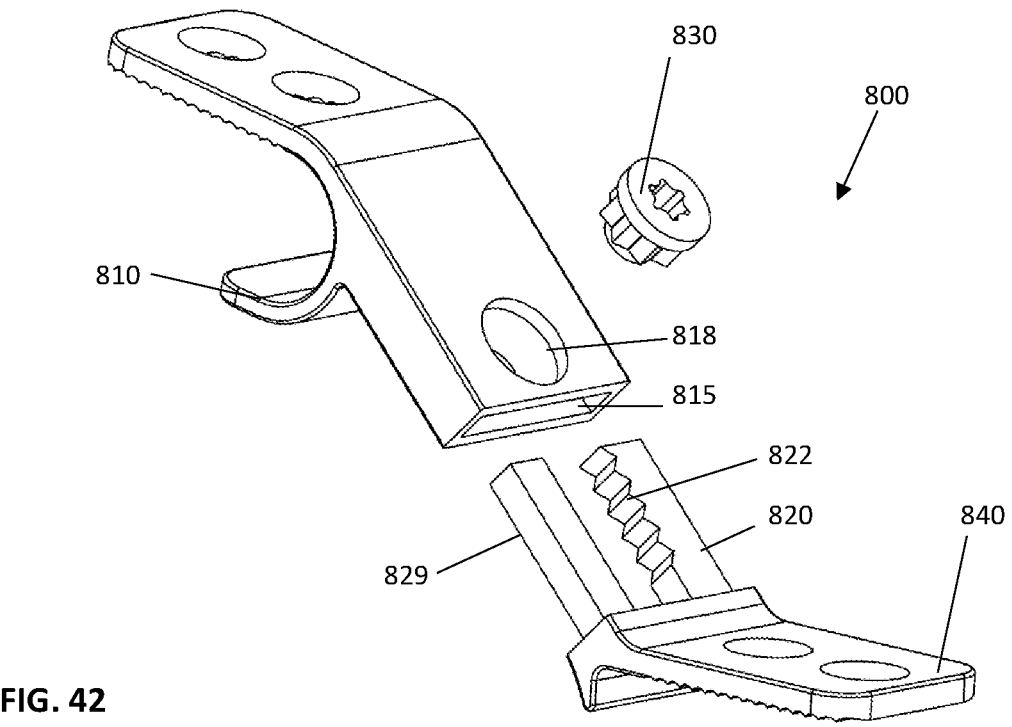
FIG. 42 is an exploded front perspective view of the eighth embodiment and component parts.
Figure 43:
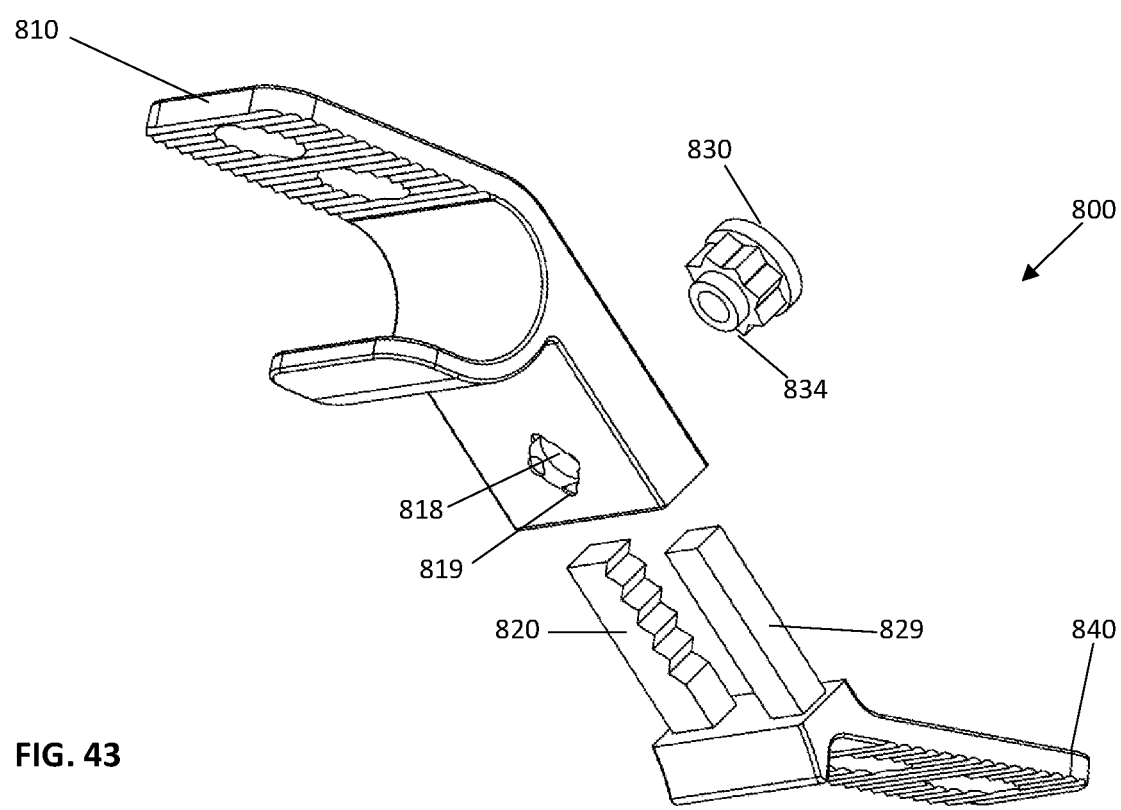
FIG. 43 is an exploded bottom perspective view of the eighth embodiment and component parts.

An eighth embodiment is shown in FIGS. 40-43 wherein the pair of posts 820, 829 are configured on the inferior plate 840 and the superior plate 810 has the channel 815 for receiving the pair of posts 820, 829 and an opening 818 for receiving the gear mechanism 830. The gear mechanism 830 is held in the opening 818 of the superior plate 810 when the cylindrical portion 834 of the gear 830 is pressed or swaged to the recesses or cavities 819 in the opening 818. The gear mechanism 830 is positioned between the pair of posts 820, 829 in such a way that the gear mechanism 830 can move the superior plate 810 relative to the inferior plate 840 by rotation of the pinion gear mechanism 830. The exploded views of FIGS. 42 and 43 show this eighth embodiment 800.

As shown, all of the configurations have a common feature in that they have a gear turning mechanism that allows the superior plate to be moved relative to the inferior plate such that the surgeon can selectively achieve the amount of expansion and opening in the spinal canal by movement of the gear mechanism to increase or decrease the amount of space between the superior plate and the inferior plate. As illustrated, all of the embodiments have a pair of openings 70 in the superior plate and the inferior plate for attachment to the lamina and lateral mass respectively using threaded fasteners 90, shown in FIGS. 1-3. When the fasteners 90 secure the plates to the vertebra the surgeon can make any adjustments to the spinal cord opening with the expandable laminoplasty device. Generally, the surgeon will already have established the exact opening size and will have moved the device to that configuration which will permit the spinal cavity to be opened the amount the surgeon desired. What is most beneficial of the present invention is that all of the embodiments provide a continuous movement in that the selection of the amount of opening and distance between the superior plate and the inferior plate can be selected without any ratchet or discrete placement limiting the adjustment capability of the surgeon. Ideally, these adjustments can be fine tuned so the surgeon can most precisely in this critical area of the neck provide the necessary relief the patient is looking for when receiving a laminoplasty procedure using the present invention expandable laminoplasty device.

The laminoplasty device components of the present invention may be made of any suitable biocompatible material including titanium, stainless steel, PEEK (polyether ether ketone), bioabsorbable plastics or any combination of such materials.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

What is claimed is:

1. An expandable laminoplasty device comprising:
    a superior plate;
    an inferior plate;
    a racked gear post having a plurality of gear teeth, the racked gear post affixed to one of the superior plate or the inferior plate;
    a pinion gear, the pinion gear having a plurality of gear teeth configured to engage the gear teeth of the racked gear post, the pinion gear being held in one of the superior plate or inferior plate not affixed to the racked gear post, wherein the superior plate or inferior plate not affixed to the racked gear post has an end with a slot or channel to receive the racked gear post and a side opening to receive and hold the pinion gear;
    wherein the rotation of the pinion gear engages the gear teeth of the racked gear post thereby coupling the superior plate to the inferior plate to form the expandable laminoplasty device, rotation of the pinion gear causes relative movement of the superior plate and inferior plate from contracted to expanded positions wherein stopping the rotation of the pinion gear fixes an amount of linear expansion between the superior and inferior plates; and
    wherein the assembly includes a second post spaced from the racked gear post, wherein the racked gear post has the gear teeth facing inwardly and the pinion gear is positioned in an central location on one of either the superior plate or inferior plate to expand or contract the assembly.

2. The expandable laminoplasty device of claim 1, wherein the second post has a rectangular or square cross section.

3. The expandable laminoplasty device of claim 1, wherein the second post has four flat sides.

4. The expandable laminoplasty device of claim 1, wherein the second post and the racked gear post are received within the slot or channel of the inferior or superior plate and prevents rotation of the two plates while allowing linear movement by the rotation of the pinion gear.

5. A method of performing a laminoplasty comprises the steps of:
    preparing a cervical vertebra by cutting through a lamina and partially cutting through the lamina at a spaced second location;
    providing an expandable laminoplasty device having:
        a superior plate;
        an inferior plate;
        a racked gear post having a plurality of gear teeth, the racked gear post affixed to one of the superior plate or the inferior plate;
        a pinion gear, the pinion gear having a plurality of gear teeth configured to engage the gear teeth of the racked gear post, the pinion gear being held in one of the superior plate or inferior plate not affixed to the racked gear post, wherein the superior plate or inferior plate not affixed to the racked gear post has an end with a slot or channel to receive the racked gear post and a side opening to receive and hold the pinion gear; and
    wherein the assembly includes a second post spaced from the racked gear post, wherein the racked gear post has the gear teeth facing inwardly and the gear is positioned in an central location on one of either the superior plate or inferior plate to expand or contract the assembly;
    wherein the rotation of the pinion gear engages the gear teeth of the racked gear post thereby coupling the superior plate to the inferior plate to form the expandable laminoplasty device, rotation of the pinion gear causes relative movement of the superior plate and inferior plate from contracted to expanded positions wherein stopping the rotation of the pinion gear fixes an amount of linear expansion between the superior and inferior plates;

positioning the expandable laminoplasty device in a contracted position with a hooked end of the superior plated on the cut lamina and the inferior plate on the lateral mass of the vertebra;

fastening ends of both superior and inferior plates to the cut lamina and the lateral mass respectively using fasteners; and rotating the pinion gear to expand the expandable laminoplasty device to a location enlarging a spinal canal opening of the vertebra completing the laminoplasty.

* * * * *